United States Patent [19]
Ouchi

[11] Patent Number: 5,899,850
[45] Date of Patent: May 4, 1999

[54] TREATMENT ACCESSORIES FOR AN ENDOSCOPE

[75] Inventor: Teruo Ouchi, Tokyo, Japan

[73] Assignee: Asahi Kogaku Kogyo Kabushiki Kaisha, Tokyo, Japan

[21] Appl. No.: 08/826,512

[22] Filed: Apr. 3, 1997

[51] Int. Cl.⁶ ............................................. A61B 1/00
[52] U.S. Cl. .................... 600/104; 600/569; 600/123
[58] Field of Search ...................... 600/104, 114, 600/121, 123, 153, 154, 569; 606/127, 131, 159, 161, 205, 206, 207, 208

[56] References Cited

U.S. PATENT DOCUMENTS

| | | | |
|---|---|---|---|
| 4,108,162 | 8/1978 | Chikashige et al. . | |
| 4,178,810 | 12/1979 | Takahashi . | |
| 4,227,537 | 10/1980 | Suciu et al. ............................ | 600/569 |
| 4,271,845 | 6/1981 | Chikashige et al. . | |
| 4,668,226 | 5/1987 | Omata et al. ......................... | 600/104 X |
| 4,759,376 | 7/1988 | Stormby ................................ | 600/569 |
| 4,966,162 | 10/1990 | Wang ..................................... | 128/750 |
| 5,201,323 | 4/1993 | Vermeulen ............................. | 128/756 |
| 5,297,560 | 3/1994 | Meduri ................................... | 600/569 |
| 5,427,115 | 6/1995 | Rowland et al. ...................... | 600/569 |
| 5,456,265 | 10/1995 | Yim ........................................ | 600/569 |
| 5,702,344 | 12/1997 | Silverstein ............................ | 600/123 X |

FOREIGN PATENT DOCUMENTS

| | | |
|---|---|---|
| 0031228 | 7/1981 | European Pat. Off. . |
| 3-10730 | 3/1991 | Japan . |
| 6-26245 | 7/1994 | Japan . |

OTHER PUBLICATIONS

"Gastrointestinal Endoscopy", Martin B. Grossman, M.D., *Clinical Symposia*, vol. 32, No. 3, CIBA Pharmaceutical Company, Summit, New Jersey, 1980.

*Primary Examiner*—Beverly M. Flanagan
*Attorney, Agent, or Firm*—Greenblum & Bernstein, P.L.C.

[57] ABSTRACT

A treatment apparatus for insertion in a forceps channel of an endoscope. The treatment apparatus includes a treatment instrument, a flexible element, and a cover tube. The flexible element is slidable within the cover tube and the treatment instrument is provided at a distal end of the flexible instrument. A distal end of the cover tube expands to receive the treatment instrument as the flexible element is drawn toward a proximal end of the cover tube. The treatment device may include a connecting instrument that supports the cover tube within the forceps channel and seals a proximal end of the forceps channel.

28 Claims, 20 Drawing Sheets

TREATMENT ACCESSORIES FOR AN ENDOSCOPE

BACKGROUND OF THE INVENTION

The present invention relates to treatment accessories that are inserted into a forceps channel of an endoscope and are used for treating an affected part on human tissue or the like.

One such treatment accessory is a cytology brush used for collecting cells inside a human body.

The process of brushing cytology is well known. In this process, a brush instrument is used to brush mucous or the like in order to collect cells or the like on bristles of the brush instrument. According to a conventional endoscope structure, when withdrawing a brush instrument through a forceps channel of the endoscope, cells that have adhered on the brush may be scraped or knocked off of the bristles either at the inlet of the forceps channel or within the forceps channel itself.

In order to avoid the problem above, a brush instrument provided with a cover tube may be used. In such a brush instrument, a brush portion having bristles is arranged to be movable in relation to the cover tube so that the brush portion can be projected from or retracted inside the cover tube. When cell are to be collected, the brush portion is projected from the cover tube, brushed against the human tissue to collect the cells, and then retracted inside the cover tube. After the brush portion is retracted inside the cover tube, the brush instrument (i.e., the brush portion and the cover tube) is retracted through the forceps channel.

However, when the mucous is brushed and mixture of the cells and the mucous adheres on the bristles of the brush, some cells are sandwiched among the bristles, while other cells remain near the outer tips of the bristles, such that, even with the cover tube, the cells near the tips of the bristles may be scraped off by the end of the cover tube when the brush is retracted inside the cover tube. Therefore, even using the brush instrument having the cover tube, it is difficult to obtain a relatively great amount of cells at a time.

In such a brush instrument, this problem could be avoided by arranging the brush instrument such that a diameter of the brush portion, including the bristles, is less than the diameter of the cover tube. However, if a smaller brush diameter is used, the amount of cells collected in one brushing operation is relatively small, and it may be difficult to obtain a sufficient amount of cells in one brushing operation.

If another instrument such as a grasping forceps instrument is used as the treatment accessory, a similar problem arises. That is, when forceps that are grasping a mucous or tissue are retracted in the forceps channel, a part of the mucous or tissue may be knocked off by the end of the forceps channel. Even if the cover tube is employed, a similar problem as discussed above occurs.

SUMMARY OF THE INVENTION

It is therefore an object of the present invention to provide an improved treatment accessory for an endoscope which can be used to obtain a larger amount of material, such as cells, in one operation.

According to one aspect of the invention, there is provided a treatment apparatus for use with an endoscope, in particular, to be inserted into a forceps channel of the endoscope. The treatment apparatus includes a flexible element, a treatment instrument connected to a distal end of the flexible element, and a cover tube having distal and proximal ends. The treatment instrument and flexible element are slidably received in the cover tube and the distal end of the cover tube expands to receive the treatment instrument.

Since the distal end of the cover tube expands to receive the treatment instrument, there is less chance that collected material will be knocked off of the treatment instrument by the cover tube. Further, the cover tube then protects the treatment instrument, and any collected material, as the cover tube and treatment instrument are drawn through the forceps channel.

In a particular case, the treatment instrument may be a cytology brush. In this case, the cytology brush preferably includes a bristle portion having bristles, a proximal end adjacent to the flexible element, and a distal end and the diameter of the bristles at the proximal end are larger than the diameter of the bristles at the distal end.

By providing larger diameter bristles at the proximal end of the bristle portion, as the cytology brush is drawn into the cover tube, the cover tube is expanded by the larger diameter bristles and thus the smaller diameter bristles do not contact the cover tube and thereby there is less chance that collected material will be knocked off.

In another particular case, the treatment instrument may be a forceps.

In a preferred embodiment, the distal end of the cover tube may include at least one longitudinally extending slit. Preferably, the length of the at least one longitudinally extending slit is longer than the length of the treatment instrument.

Alternatively, the distal end of the cover tube may include a plurality of longitudinally extending slits. For example, the distal end of the cover tube may include three longitudinally extending slits or four longitudinally extending slits.

If a plurality of sufficiently long slits are provided, as the treatment instrument is drawn into the cover tube, the cover tube opens like a flower to receive the treatment instrument with minimal contact and then, as the cover tube and treatment instrument are drawn into the forceps channel, the cover tube folds over the treatment instrument to provide protection as the cover tube and treatment instrument are drawn through the forceps channel.

In another embodiment, the diameter of the distal end of the cover tube is larger than the diameter of the remainder of the cover tube. Preferably, the distal end of the cover tube includes at least one longitudinally extending slit.

In yet another embodiment, the distal end of the cover tube may include at least one fold and the at least one fold allows the distal end of the cover tube to expand. In particular, the distal end of the covers tube may be funnel-shaped when expanded.

In yet another embodiment, the treatment apparatus may further include a sheath surrounding the flexible element such that the sheath locates the flexible element at substantially the radial center of the cover tube. Preferably, the sheath is of a material having a low friction coefficient. The sheath may extend along substantially the entire length of the flexible element or be provided at only a distal end portion of the flexible element.

The provision of a sheath ensures that the treatment instrument is drawn into the center of the cover tube as opposed to being drawn into the cover tube such that the treatment instrument may catch at an edge of the opening to the cover tube, which may cause difficulties in the removal of the treatment instrument or may cause the collected material to be knocked loose.

According to yet another embodiment, the treatment apparatus may further include a connecting instrument for insertion into the forceps channel, the treatment instrument, flexible element, and cover tube being inserted into a throat portion of the connecting instrument.

In this embodiment, an inner diameter of the throat portion is preferably less than an outer diameter of the cover tube, whereby a predetermined amount of friction exists between the outer surface of the cover tube and the inner surface of the throat portion.

Alternatively, the throat portion may have an oval cross-sectional shape and the cover tube may have a circular cross-sectional shape such that a predetermined amount of friction exists between the outer surface of the cover tube and the inner surface of the throat portion.

In this embodiment, the connecting instrument may further include a treatment instrument accommodation portion that has a greater diameter than a diameter of the treatment instrument.

The provision of the connecting instrument allows the treatment instrument, flexible element, and cover tube to be easily and quickly inserted into the forceps channel of the endoscope. The connecting instrument may further support the cover tube at a particular position in relation to the forceps channel and prevent the release of any liquids or the like from within the forceps channel.

According to another aspect of the invention, there is provided a connecting instrument for use with an endoscope. The connecting instrument is inserted into a forceps channel of the endoscope for receipt of a treatment instrument, a flexible element, a cover tube. The treatment instrument is connected to the flexible element and the flexible element is surrounded by the cover tube. In particular, the connecting instrument includes a throat portion for receipt of the treatment instrument, flexible element, and cover tube being inserted into a throat portion of the connecting instrument.

Preferably, an inner diameter of the throat portion is less than an outer diameter of the cover tube, whereby a predetermined amount of friction exists between the outer surface of the cover tube and the inner surface of the throat portion.

Alternatively, the throat portion may have an oval cross-sectional shape and the cover tube may have a circular cross-sectional shape such that a predetermined amount of friction exists between the outer surface of the cover tube and the inner surface of the throat portion.

The connecting instrument may further include a treatment instrument accommodation portion that has a diameter greater than a diameter of the treatment instrument.

DETAILED DESCRIPTION OF THE PREFERRED EMBODIMENTS

Figure 1:
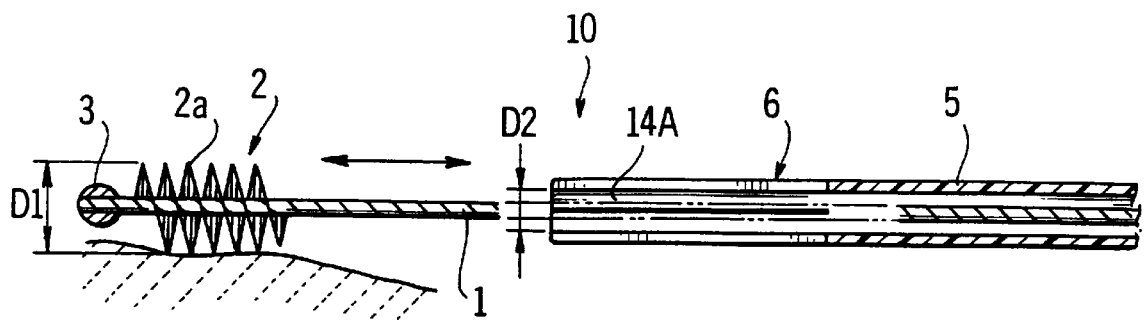
FIG. 1 is a schematic sectional side view of a cytology brush instrument according to a first embodiment.

FIG. 1 shows a schematic sectional side view of a cytology brush instrument 10 according to a first embodiment. The cytology brush instrument 10 is a treatment accessory for an endoscope, that, in use, is inserted through a forceps channel of the endoscope. The brush instrument 10 has a brush portion 2 that includes a plurality of bristles 2a extending radially at the tip of an operation wire 1. The operation wire 1 is a flexible wire which is formed by, for example, twisting strands of stainless steel wire. A ball-shaped member 3 is provided at the distal end of the operation wire 1.

Figure 3:
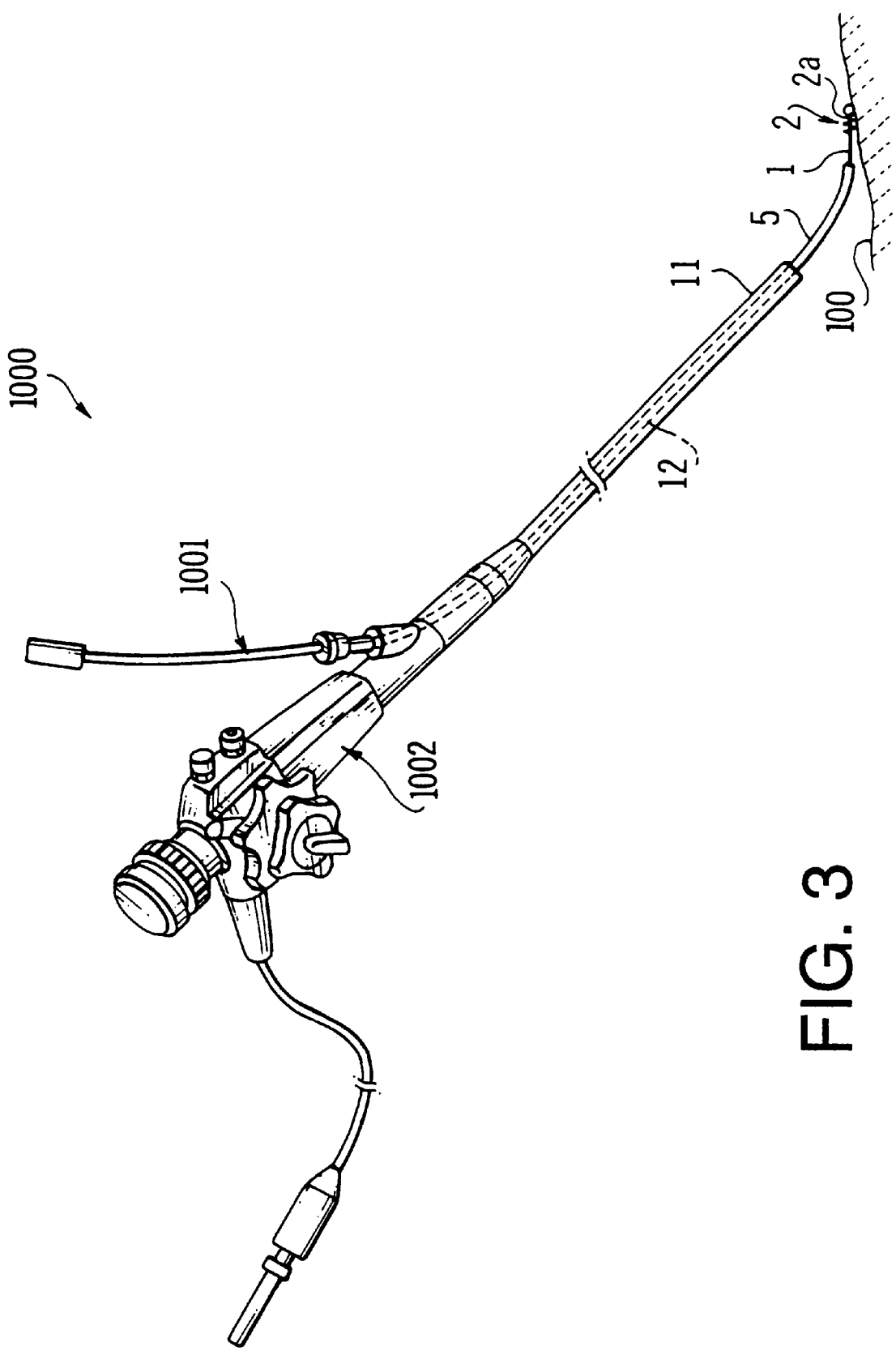
FIG. 3 is a perspective view of an endoscope having a forceps channel in which the cytology brush instrument of FIG. 1 is inserted.

The cytology brush instrument 10 is also provided with a cover tube 5. The cover tube 5 is a flexible tube having elasticity an is made of, for example, fluorocarbon resin. The operation wire 1 is threaded through the inside of the cover tube 5. As shown in FIG. 3, the cover tube 5 is inserted in a forceps channel 12 of an endoscope 1000. The forceps channel 12 extends from a tip of an insertion part 11 of the endoscope 1000 to a manipulation part 1002 of the endoscope 1000. By manipulating the operation wire 1 using an operating unit 1001 provided at the manipulation part 1002 of the endoscope 1000, an operator of the endoscope 1000 can move the brush portion 2 along a direction of the axis of the operation wire 1 at the bristles 2a.

Figure 2A:
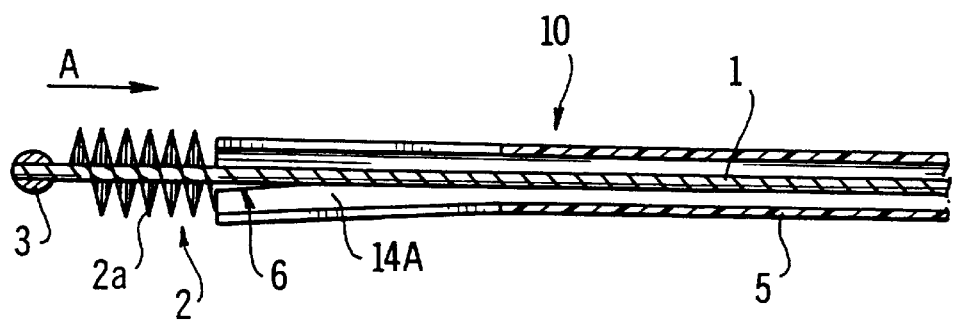
FIGS. 2A and 2B are schematic sectional side views of the cytology brush instrument of FIG. 1 showing a brush portion being drawn inside a cover tube.
Figure 2B:
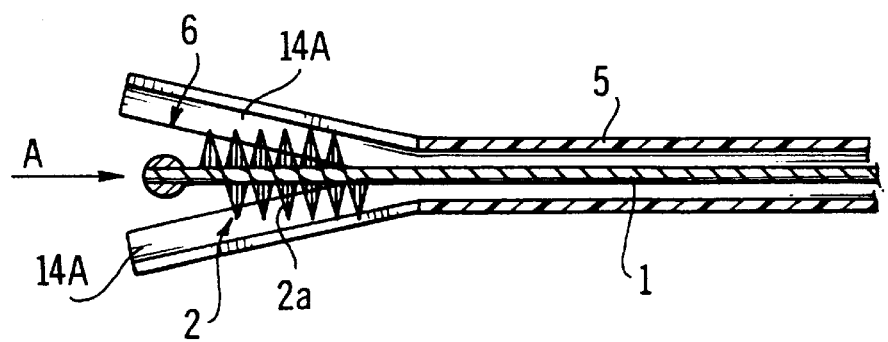

Referring to FIGS. 1, 2A and 2B, the distal end of the cover tube 5 is formed to have a plurality of slits 6 extending a predetermined length from the distal end of the cover tube 5. In the first embodiment, there are four slits 6 extending in the longitudinal direction of the cover tube 5. The slits 6 are arranged substantially 90 degrees apart from each other, in the circumferential direction. The length of each slit 6 is longer than the length, in the axial direction, of the brush portion 2, as shown in FIGS. 2A and 2B. Note that the four slits 6 divide the distal end portion of the cover tube 5 into four openable portions 14A.

Further, in the first embodiment, the outer diameter D1 of the brush portion 2 including the length of the bristles 2a is greater than the inner diameter D2 of the distal end of the cover tube 5, that is, D1>D2.

As shown in FIGS. 1, 2A, 2B, and 3, in operation, the cytology brush instrument 10 is inserted through the forceps channel 12. The brush portion 2 is protruded from the distal end of the cover tube 5 and pushed against mucous 100 inside a human body. The operation wire 1 is then moved or rotated such that cells at the surface of the mucous 100 are dislodged by the brush portion 2. Some cells, as well as the mucous, are sandwiched among the bristles 2a, and other cells, together with the mucous, adhere to the tips of the bristles 2a.

Next, the operation wire 1 is pulled by the operator, i.e., moved in the direction indicated by arrow A in FIG. 2A, and the brush portion 2 is drawn inside the distal end portion of the cover tube 5.

When the brush portion 2 is about to enter the distal end portion of the cover tube (as shown in FIG. 2A), since the diameter D1 of the brush portion 2 is greater than the inner diameter D2 of the cover tube 5, the distal end portion of the cover tube 5 is opened (pushed apart) by the brush portion 2 (i.e., by the bristles 2a). In the first embodiment, the bristles 2a of the brush portion 2 are arranged to form a spiral. Accordingly, as the brush portion 2 enters the cover tube 5, the openable portions 14A of the cover tube 5, which are divided by the slits 6, are opened sequentially such that there is very little resistance to the pulling of the operation wire 1 in the direction of the arrow A.

Figure 4:
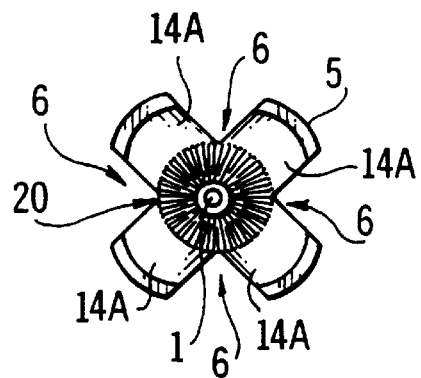
FIG. 4 is a schematic end view of the cytology brush instrument of FIG. 1;.

By further pulling the brush portion 2 in the direction of the arrow A, the brush portion 2 fully enters the cover tube 5 as shown FIG. 2B. As shown in FIGS. 2A, 2B and 4, when the brush portion 2 is located inside the end portion of the cover tube 5, the openable portions 14A of the cover tube 5 open like a flower petal due to the four slits 6.

Since the end portion of the cover tube 5 opens widely when the brush portion 2 is retracted inside the end portion of the cover tube 5, the cells adhering on the brush portion 2 are not as easily scraped off by the end of the cover tube 5.

Figure 5:
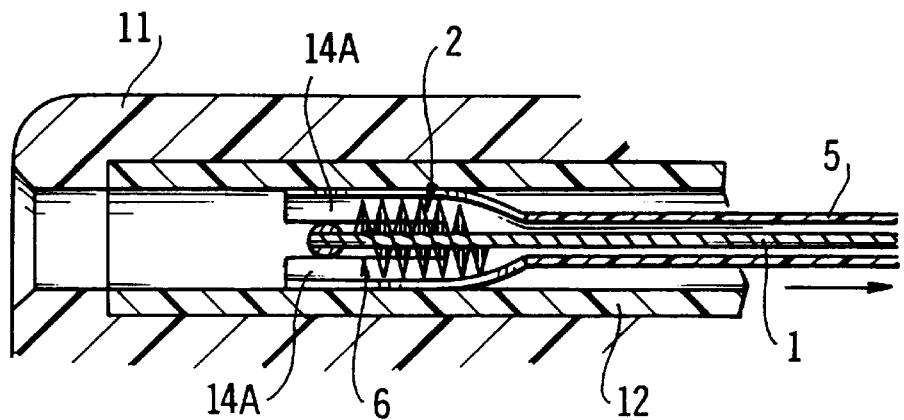
FIG. 5 is a schematic sectional side view of the cytology brush instrument of FIG. 1 when inside a forceps channel.

As shown in FIG. 5, once the brush portion 2 is inside the end of the cover tube 5, the cover tube 5 is retracted inside the forceps channel 12 at the insertion part 11 of the endoscope 1000.

When the cover tube 5 is retracted inside, the forceps channel 12, the openable portions 14A of the cover tube 5 which were opened like a flower petal fold to fit the inner surface of the forceps channel 12 and cover the brush portion 2. With this structure, the brush portion 2 retains a large number of cells as it is drawn to the manipulation part 1002 of the endoscope 1000 through the forceps channel 12.

Figure 6:
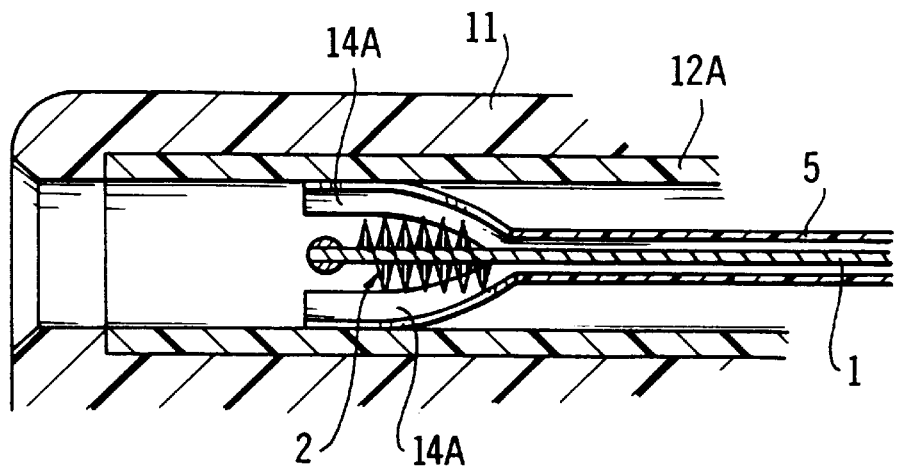
FIG. 6 is a schematic sectional side view of the cytology brush instrument of FIG. 1 when inside a larger forceps channel than that of FIG. 5.
Figure 7:
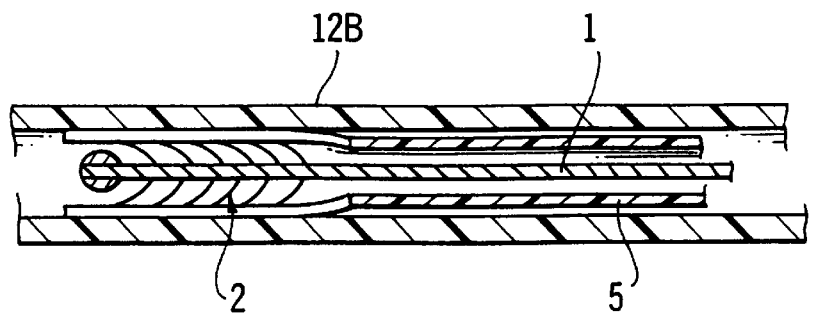
FIG. 7 is a schematic sectional side view of the cytology brush instrument of FIG. 1 when inside a smaller forceps channel than that of FIG. 5.

FIG. 6 shows the brush instrument 10 inserted in a forceps channel 12A which has a greater inner diameter than the forceps channel 12 shown in FIG. 5. In this case, the brush portion 2 may convey more cells in comparison with the case shown in FIG. 5 since there will be less contact between the bristles 2a and the cover tube 5. However note that, with the brush instrument 10 according to the first embodiment, the brush portion 2 maximizes the number of cells conveyed for a given diameter of the forceps channel 12, 12A. Further, FIG. 7 shows a forceps channel 12B which has a smaller diameter than the forceps channel 12 shown in FIG. 5. Also in this case, the brush portion 2 maximizes the amount of cells conveyed for the forceps channel 12B. That is, when the brush instrument 10 is inserted in the forceps channel 12B, since the brush portion 2 has already been retracted inside the end portion of the cover tube 5, the brush portion 2 does not directly contact the end of the forceps channel 12B, and the amount of cells scraped off by the end of the forceps channel 12B is minimized.

Figure 8:
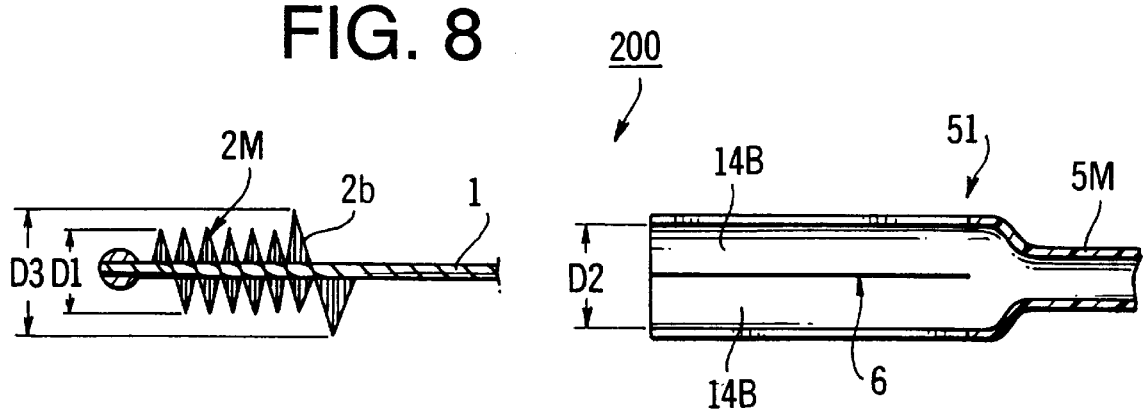
FIG. 8 is a schematic sectional side view of a cover tube and a brush part of a cytology brush instrument according to a second embodiment.
Figure 9:
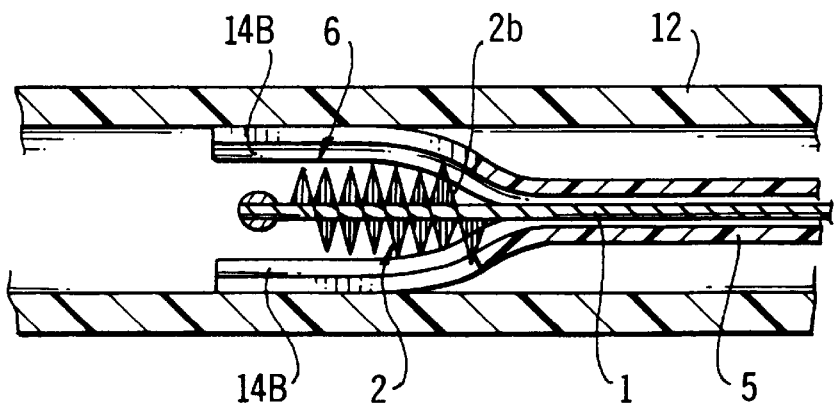
FIG. 9 is a schematic sectional side view of the cytology brush instrument of FIG. 8 when inside a forceps channel.

FIG. 8 shows a cytology brush instrument 200 including a brush portion 2M and a cover tube 5M according to a second embodiment. In the second embodiment, the brush portion 2M is provided with large bristles 2b at the manipulation side end of the brush portion 2M that have a larger diameter D3 than the diameter D1 of the bristles 2a. Further, the distal end of the cover tube 5M is provided with an enlarged diameter portion 51 in which the brush portion 2M is to be accommodated. The enlarged diameter portion 51 has an inner diameter D2 that is larger than the diameter D1 of the bristles 2a, and similar to the first embodiment, is formed with four slits 6 with divides the enlarged diameter portion 51 into four openable portions 14B.

With the cover tube 5M and the brush portion 2M constructed as described above, as the cover tube 5M is drawn into the forceps channel 12, the enlarged diameter portion 51 of the cover tube 5M folds similar to the cover tube 5 of the first embodiment and the large bristles 2b of the brush portion 2M keep the enlarged diameter portion 51 of the cover tube 5M relatively wide apart such that there is less contact between the bristles 2a and the cover tube 5M. Therefore, the amount of cells conveyed by the brush portion 2M is increased.

It is noted that, in the above-described first and second embodiments, although the bristles 2a, 2b are directly fixed on the operation wire 1, the structure does not need to be limited in this manner. For example, a structure in which a brush is connected with the operation wire 1 by a connecting member could be used.

Further, it is not essential that the cover tube 5 or 5M has the same amount of flexibility throughout its length, a flexible formation of at least the distal end portion (i.e., the openable portions 14A, 14B) of the cover tube 5 or 5M will achieve the same result. Also, the cover tube 5 can be made from a variety of materials such as polyethylene, polyurethane, polyimide or the like and the number of slits 6 formed at the distal end of the cover tube 5 is not limited to four, but may be any number greater than one.

According to the first and second embodiments, the diameter D1 of the brush portion 2, 2M can be designed sufficiently large to capture a sufficient quantity of cells in a single brushing operation and the brush portion 2, 2M can enter into the cover tube 5, 5M in a way such that the cells collected by the brush portion 2, 2M are not as easily scraped off by the end of the cover tube 5, 5M.

Figure 10:
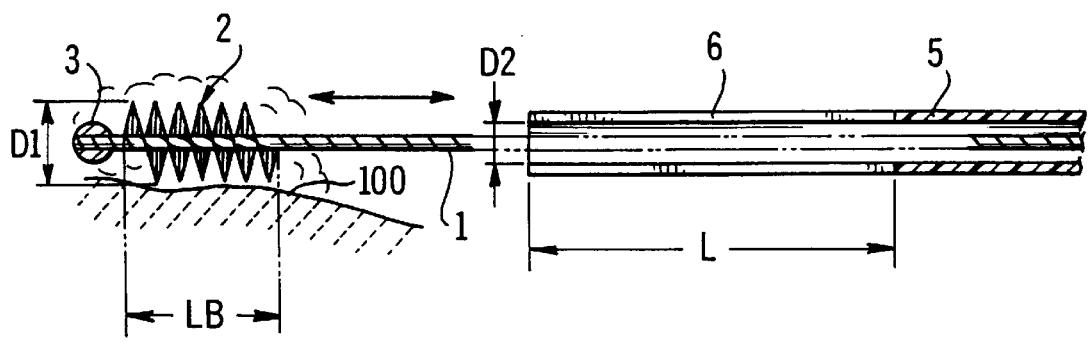
FIG. 10 is a schematic sectional side view of the cytology brush instrument of FIG. 1.

In the above-described first and second embodiments, in order to obtain good performance in terms of the collection of the cells and the opening/closing of the slitted end portion (i.e., the openable portions 14A, 14B) of the cover tube 5, 5M, it is preferable to form the slits 6 to have a length L which is from 1.5 to 2.5 as long as a length LB of the brush portion 2, 2M (see FIG. 10). As shown in FIG. 10, using the brush instrument 10 of the first embodiment as an example, the length LB of the brush portion 2 in the direction of the operation wire 1 is approximately half of the length L of the slits 6.

Figure 11:
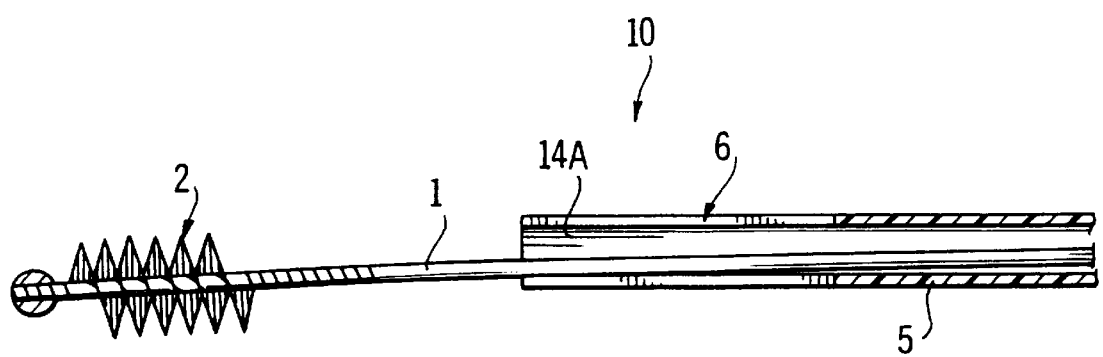
FIG. 11 is a schematic sectional side view of the cytology brush instrument of FIG. 1.

In the above-described first and second embodiments, if the inner diameter of the cover tube 5 is greater than the diameter of the operation wire 1 as shown in FIG. 11, a relatively large space is formed between the operation wire 1 and the inner surface of the cover tube 5. In such a case, the position of the operation wire 1 in the cover tube 5 may shift depending on a condition of use, for example, due to gravity, a bend in the operation wire 1, twisting of the operation wire 1 and the like. If such shifting occurs, as the brush portion 2 is retracted into the cover tube 5, the brush portion 2 may catch on an edge of the opening of the cover tube 5, thereby causing increased resistance when the operation wire 1 is pulled (moved in the right-hand direction in FIG. 11) relative to the cover tube 5. Further, as the brush portion 2 is retracted inside the cover tube 5, the brush portion 2 rubs against the edge of the opening of the cover tube 5 (i.e., the edges of the openable portions 14A), and the amount of the cells collected is decreased.

Figure 12:
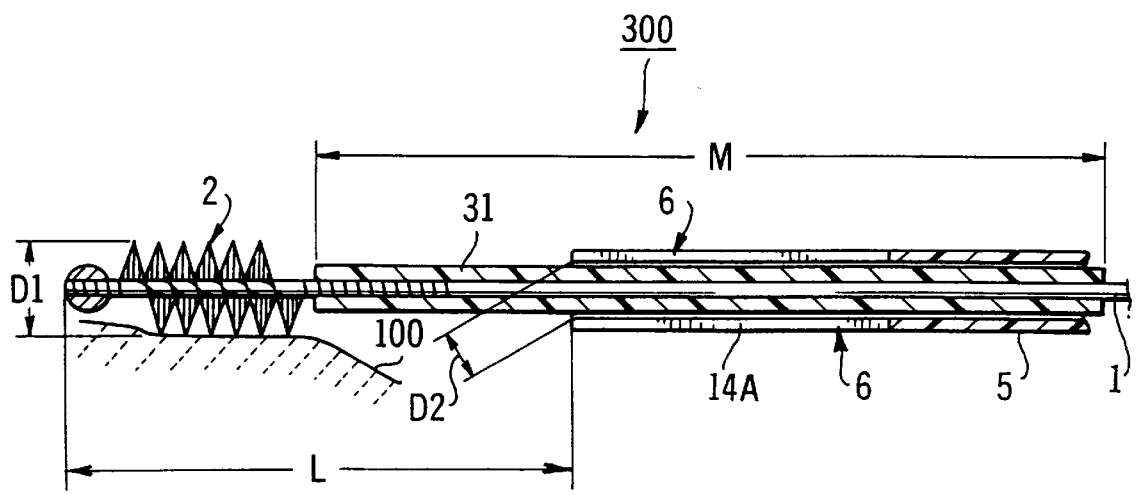
FIG. 12 is a schematic sectional side view of a cytology brush instrument according to a third embodiment.

FIG. 12 shows a cytology brush instrument 300 according to a third embodiment of the invention to handle the case when the inner diameter of the cover tube 5 is larger than the diameter of the operation wire 1. The cytology brush instrument 300 has a similar structure to that of the first embodiment shown in FIG. 1. In the third embodiment, the cytology brush instrument 300 is further provided with a sheath 31 having a length M surrounding the operation wire 1. It should be noted that elements of the cytology brush instrument 300 that are the same as those of the first embodiment are given the same reference numerals and the description thereof will be omitted.

In FIG. 12, a distance L represents the maximum distance between the distal end of the brush portion 2 and the distal end of the cover tube 5 when the brush portion 2 is fully extended from the cover tube 5.

Figure 13:
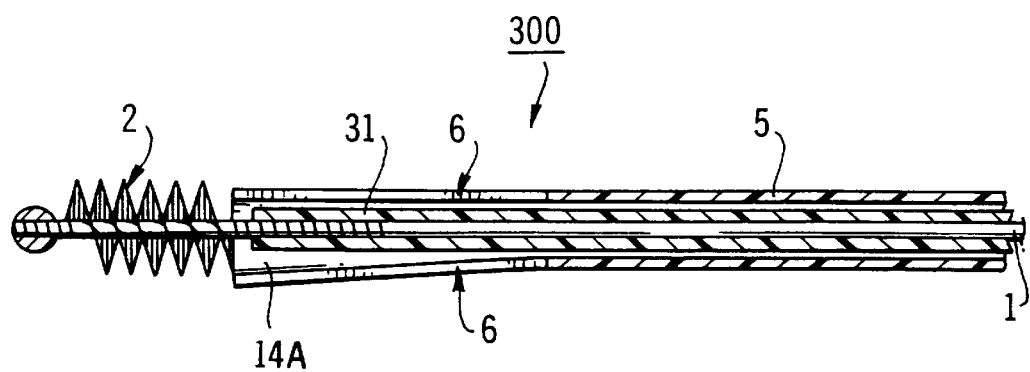
FIG. 13 is a schematic sectional side view of the cytology brush instrument of FIG. 12 in a different state.

Similar to the first embodiment, the four slits 6 divide the end portion of the cover tube 5 into four openable portions 14A (see FIG. 13). Similar to the first embodiment, the length of the slits 6 and therefore the length of the openable portions 14A is greater than the length of the brush portion 2.

The sheath 31 is made of, for example, polyethylene resin, Teflon resin or the like, which are preferable since they have a relatively low friction coefficient.

The sheath 31 and the operation wire 1 are formed, for example, by forming the sheath 31 in a tubular shape, inserting the operation wire 1 therein, and then heat shrinking the sheath 31. Alternatively, the sheath 31 may be formed to have a tubular shape having a diameter smaller than that of the operation wire 1, and then forcibly inserting the operation wire 1, or further alternatively, first daubing the operation wire 1 with the resin and then drying the resin to form the sheath 31.

The thickness of the sheath 31 on the operation wire 1 is determined such that any space between the operation wire 1 and the inner surface of the cover tube 5 is filled with the sheath 31. In other words, the operation wire 1 is supported such that the operation wire 1 is always located at the center of the cover tube 5 when the operation wire 1 with the sheath 31 is inserted in the cover tube 5.

The cytology brush instrument 300 is inserted though the forceps channel 12 of a flexible insertion part 11 of an endoscope (cf. FIG. 3). In order to collect material such as cells, first the distal end of the cover tube 5 is extended from the distal end of the insertion part 11, and further, as shown in FIG. 12, the brush portion 2 is extended from the distal end of the cover tube 5. The brush portion 2 is rubbed against the human tissue (mucous) 100 in a human body cavity, and some cells and mucous on the human tissue 100 are scraped off. The cells and mucous are sandwiched among the bristles 2a of the brush portion 2 and some are held near the tips of the bristles 2a of the brush portion 2.

After the cells are scraped by the brush portion 2, the operation wire 1 is pulled such that the brush portion 2 is retracted inside the cover tube 5 (cf. FIG. 2). As the brush portion 2 is drawn inside the cover tube 5, the openable portions 14A open sequentially one after another due to the spiral arrangement of the bristles 2a of the brush portion 2, which reduces the resistance when the operation wire 1 is pulled.

Further, due to the existence of the sheath 31, the bristles 2a of the brush portion 2 apply force evenly to the openable portions 14A, and the brush portion 2 is accommodated at the center of the and portion of the cover tube 5.

As described above, since the sheath 31 is provided on the operation wire 1, retraction of the brush portion 2 in the cover tube is done smoothly, and further, the openable portions 14A of the cover tube 5 are opened evenly, the brush portion 2 is not overly squeezed by the end of the cover tube 5 and the collected cells are not scraped or knocked off of the brush portion 2.

Figure 14:
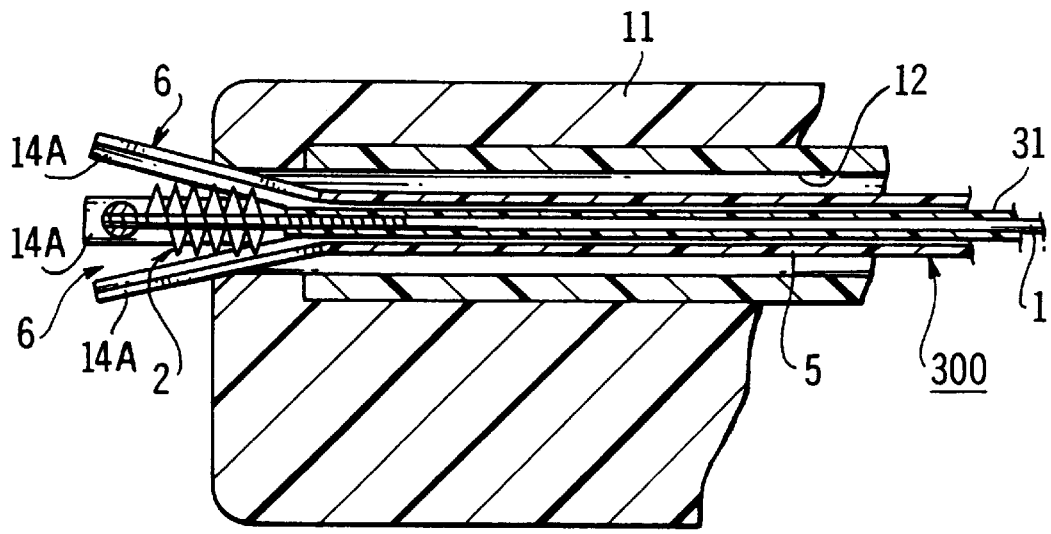
FIG. 14 is a schematic sectional side view of the cytology brush instrument of FIG. 12 when being drawn inside a forceps channel.
Figure 15:
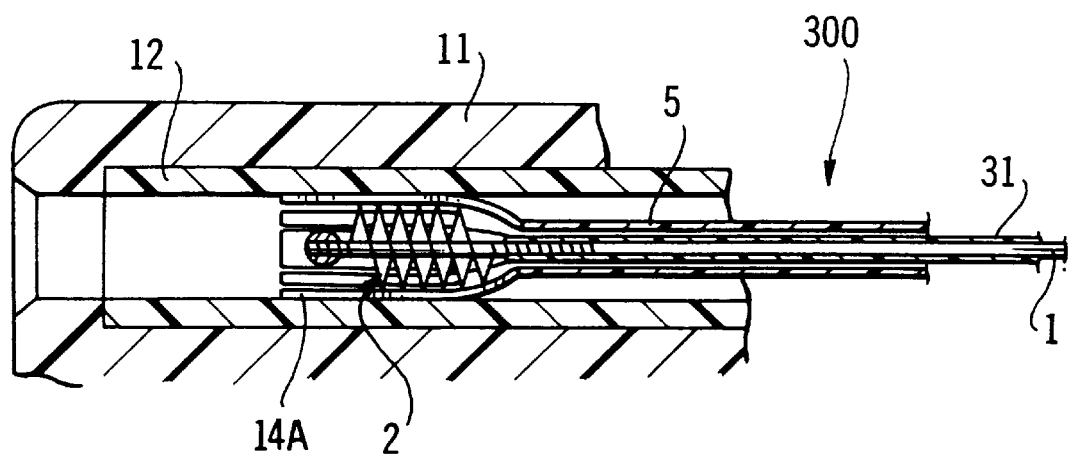
FIG. 15 is a schematic sectional side view of the cytology brush instrument of FIG. 12 when inside the forceps channel.

When the brush portion 2 has been accommodated inside the cover tube 5, the operation wire 1 and the cover tube 5 are simultaneously retracted in the forceps channel 12 of the endoscope (see FIGS. 14 and 15).

As shown in FIG. 15, when the cover tube 5 accommodating the brush portion 2 is located inside the forceps channel 12, the end of the openable portions 14A are pushed towards the brush portion 2, and the brush instrument 300 is pulled and removed from the endoscope.

Figure 16:
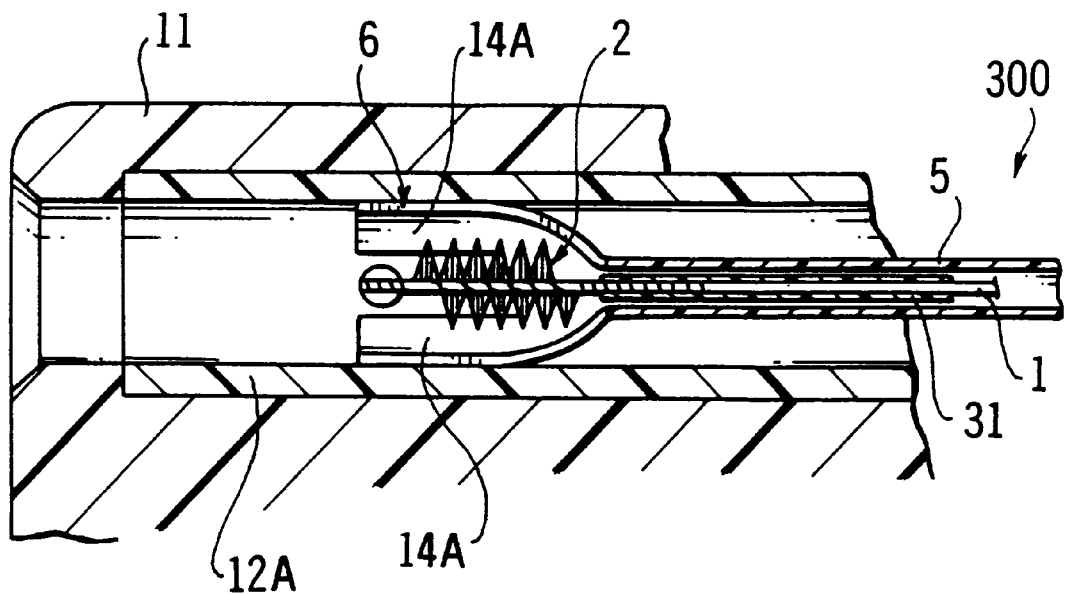
FIG. 16 is a schematic sectional side view of the cytology brush instrument of FIG. 12 when inside a larger forceps channel than that of FIG. 15.
Figure 17:
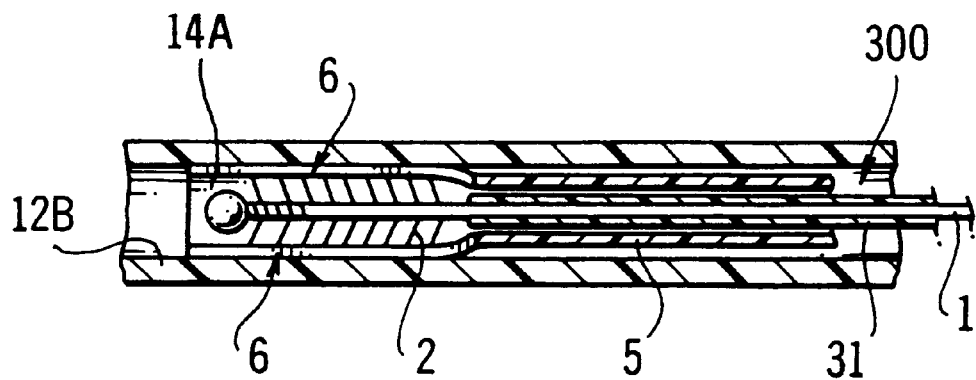
FIG. 17 is a schematic sectional side view of the cytology brush instrument of FIG. 12 when inside a smaller forceps channel than that of FIG. 15.

FIGS. 16 and 17 are similar to FIGS. 6 and 7 relating to the first embodiment. In FIG. 16, the brush instrument 300 is the same as in FIGS. 14 and 15, but is drawn into a forceps channel 12A that has a diameter that is greater than that in FIGS. 14 and 15. The description related to FIG. 6 applies to the third embodiment and further detail will be omitted. Further, in FIG. 16, since the sheath 31 is formed on the operation wire 1, the brush portion 2 is stably located at the center of the cover tube 5. Similarly, in FIG. 17, the forceps channel 12B has a smaller diameter in comparison to that shown in FIG. 14. Here also, the sheath 31 holds the brush portion 2 at the center of the cover tube 5.

As described above, the use of the sheath 31, suppresses any inclination of the brush portion with respect to the cover tube 5 regardless of the diameter of the forceps channel of the endoscope, thus, enabling the brush portion 2 to carry as many cells as possible.

Figure 18:
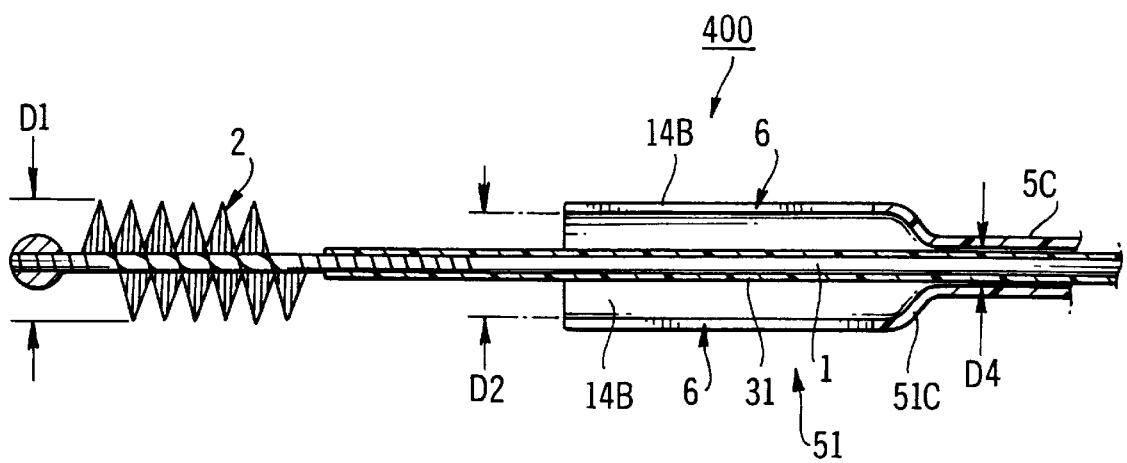
FIG. 18 is a schematic sectional side view of a cytology brush instrument according to a fourth embodiment.

FIG. 18 shows a cytology brush instrument 400 according to a fourth embodiment of the invention.

In the cytology brush instrument 400, the inner diameter D2 of a distal end portion 51 of a cover tube 5C is greater than the inner diameter D4 of the other portion of the cover tube 5C and less than the outer diameter D1 of the brush portion 2. The operating wire 1 is provided with a sheath 31 that has a diameter that is slightly less than the inner diameter D4 of the other portion of the cover tube 5C. The distal end portion 51 of the cover tube 5C is joined to the other portion of the cover tube 5C via a connecting portion 51C. A plurality of slits 6 are formed on the distal end portion 51, evenly spaced around the circumference thereof. The distal end portion 51 is divided into a plurality of openable portions 14B by the plurality of slits 6.

With this structure, when the brush portion 2 is drawn into the distal end portion 51, the amount of deformation of the cover tube 5C required is suppressed compared with that of the third embodiment, and accordingly resistance against the retracting of the brush is decreased. Further, the deformation of the openable portions 14B after the brush portion 2 has been completely accommodated in the cover tube 5C is relatively small so that the chance of the collected cells or mucous falling through the space formed between the opened openable portions 14B is reduced.

Figure 19:
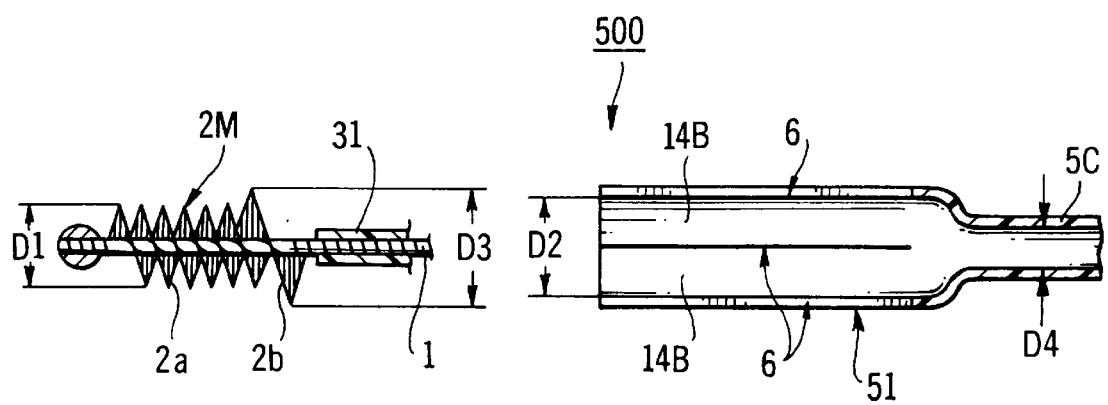
FIG. 19 is a schematic sectional side view of a cover tube and a brush part of a cytology brush instrument according to a fifth embodiment.
Figure 20:
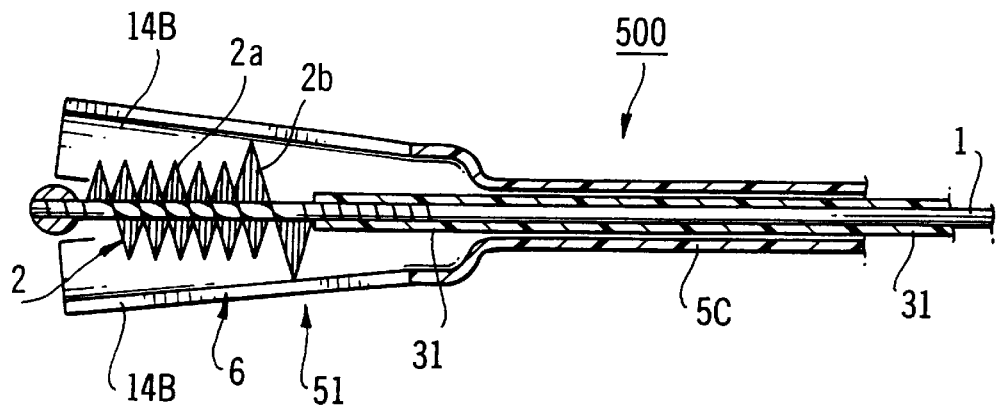
FIG. 20 is a schematic sectional side view of the cytology brush instrument of FIG. 19 in a different state.
Figure 21:
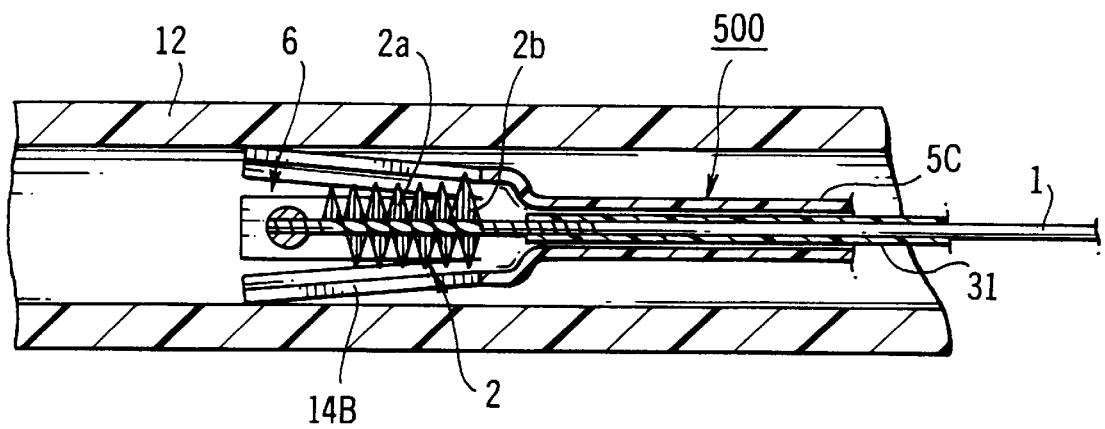
FIG. 21 is a schematic sectional side view of the cytology brush instrument of FIG. 19 when inside a forceps channel.

FIGS. 19 through 21 show a brush instrument 500 according to a fifth embodiment. The brush instrument 500 has the same structure as the brush instrument 400 shown in FIG. 18 except that a brush portion 2M is formed to have large bristles 2b, having a diameter D3, at the end that is first drawn into the cover tube 5C. The other portion of the brush portion 2 has smaller bristles 2a with a diameter D1 (cf. FIG. 8).

With this structure, as shown in FIG. 20, when the brush portion 2M is retracted inside the cover tube 5C, the openable portions 14B are pushed to open by the large bristles 2b of the brush portion 2M. After the brush portion 2M is completely accommodated in the cover tube 5C, the brush portion 2M and the end portion of the cover tube 5C are pulled inside the forceps channel 12 as shown in FIG. 21. According to the brush instrument 500, the area of the brush portion 2M which contacts the inner surface of the cover tube 5C is decreased, and there is less chance of the collected cells or mucous being knocked off of the brush portion 2M.

In the third, fourth, and fifth embodiments described above, the sheath 31 may be provided on the entire length of the operation wire 1, or alternatively, may be provided on a predetermined area adjacent to the brush portion 2 or 2M.

Figure 22:
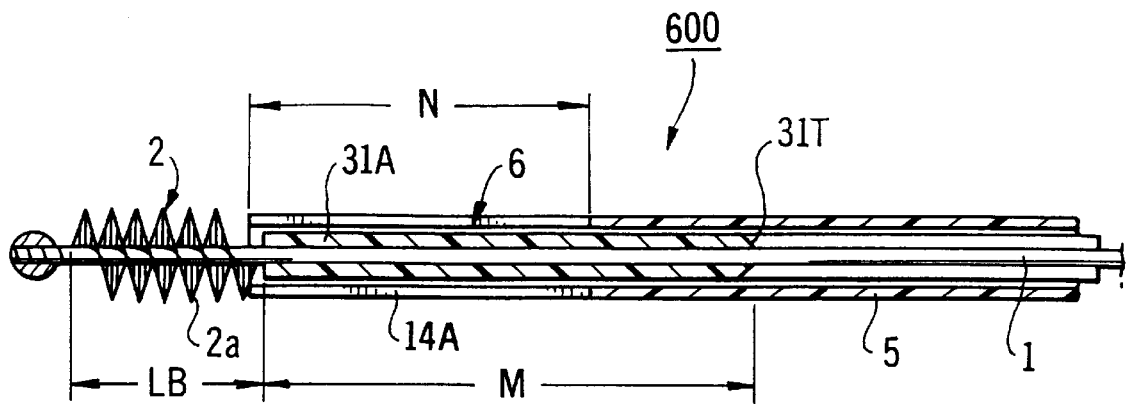
FIG. 22 is a schematic sectional side view of the cytology brush instrument according to a sixth embodiment.

FIG. 22 shows a brush instrument 600 according to a sixth embodiment. The brush instrument 600 is similar to the brush instrument 300 shown in FIG. 12 except that a sheath 31A is provided only at a predetermined portion adjacent to the brush portion 2.

The length of the sheath 31A is M, which is greater than the length LB of the brush portion 2 plus the length N of the slits 6, or the openable portions 14A. In order to allow the retraction of the brush portion 2 into the cover tube 5 to be performed easily, the proximal end of the sheath 31A is formed as a tapered portion 31T.

If the sheath 31A is formed as described above, even if the sheath 31A is moved to extend beyond the portion of the cover tube 5 where there are no slits 6, the operation wire 1 can still be retracted smoothly since the sheath 31A has the tapered portion 31T. Then, after the sheath 31M is in the portion of the cover tube 5 where there are no slits 6, the operation wire 1 is held in place such that the brush portion 2 is positioned at the center of the cover tube 5.

Figure 23A:
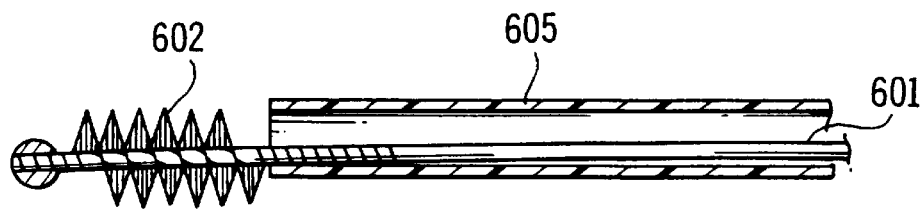
FIG. 23A is a schematic sectional side view of a conventional cytology brush instrument.

It should be noted that, the sheaths 31, 31A described above, can also be used in a conventional cover tube (i.e., one that is not provided with slits), in order to support a brush portion at the center of a conventional cover tube. FIG. 23A shows a conventional cytology brush including a brush portion 602, an operation wire 601, and a cover tube 605. The cover tube 605 is formed as a tube through which the operation wire 601, and the brush portion 602 are inserted. With this arrangement, a problem may occur in that, as shown in FIG. 23A, if the inner diameter of the cover tube 605 is greater than the diameter of the operation wire 601, there is a relatively large space between the operation wire 601 and the inner surface of the cover tube 605. In such a case, the position of the operation wire 601 in the cover tube 605 may shift depending on a condition of use, for example, due to gravity, a bend in the operation wire 601, twisting of the operation wire 601 and the like. If such shifting occurs, as the brush portion 602 is retracted into the cover tube 605, the brush portion 2 may catch on an edge of the opening of the cover tube 605, thereby causing increased resistance when the operation wire 601 is pulled (moved in the right-hand direction in FIG. 23A) relative to the cover tube 605. Further, as the brush portion 602 is retracted inside the cover tube 605, the brush portion 602 rubs against the edge of the opening of the cover tube 605, and the amount of cells collected is reduced.

Figure 23B:
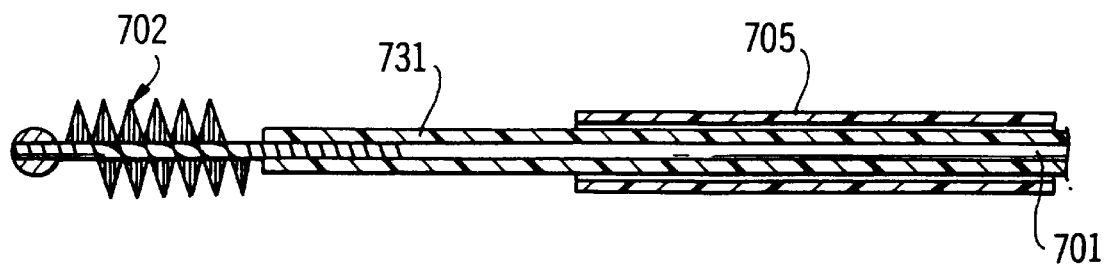
FIG. 23B is a schematic sectional side view of a cytology brush instrument according to a seventh embodiment.

FIG. 23B shows a cytology brush instrument 700 according to a seventh embodiment of the invention. The cytology brush instrument 700 has a similar structure to that of the first embodiment shown in FIG. 1, however, in the seventh embodiment, the cytology brush instrument 700 includes a cover tube 705 that is formed as a solid tube, i.e., does not have any openable portions 14A as in the first embodiment. Further, the cytology brush instrument 700 is further provided with a sheath 731 surrounding the operation wire 1. It should be noted that elements of the cytology brush instrument 700 that are the same as those of the first embodiment are given the same reference numerals and the description thereof will be omitted.

The sheath 731 is made of, for example, polyethylene resin, Teflon resin or the like, which are preferable since they have a relatively low friction coefficient.

The sheath 731 and the operation wire 1 are formed, for example, by forming the sheath 731 in a tubular shape, inserting the operation wire 1 therein, and then heat shrinking the sheath 731. Alternatively, the sheath 731 may be formed to have a tubular shape having a diameter smaller than that of the operation wire 1, and then forcibly inserting the operation wire 1, or further alternatively, first daubing the operation wire 1 with the resin and then drying the resin to form the sheath 731.

The thickness of the sheath 731 on the operation wire 1 is determined such that any space between the operation wire 1 and the inner surface of the cover tube 705 is filled with the sheath 731. In other words, the operation wire 1 is supported such that the operation wire 1 is always located at the center of the cover tube 705 when the operation wire 1 with the sheath 731 is inserted in the cover tube 705.

Further, due to the existence of the sheath 731, the brush portion 2 is accommodated at the center of the end portion of the cover tube 705.

As described above, since the sheath 731 is provided on the operation wire 1, retraction of the brush portion 2 in the cover tube 705 is done smoothly and the collected cells are not scraped or knocked off of the brush portion 2 as easily.

Further alternatively, note that it is not necessary that the sheaths 31, 31A, 731 provided on the operation wire 1 be continuous, that is, as long as the brush portion 2 is held at the center of the cover tube 5, 705, the sheaths 31, 31A, 731 may be formed as a plurality of short sheaths spaced from each other. Still further alternatively, any member which holds the operation wire 1 in place could be used in place of the sheath 31, 31A, 731.

Figure 24:
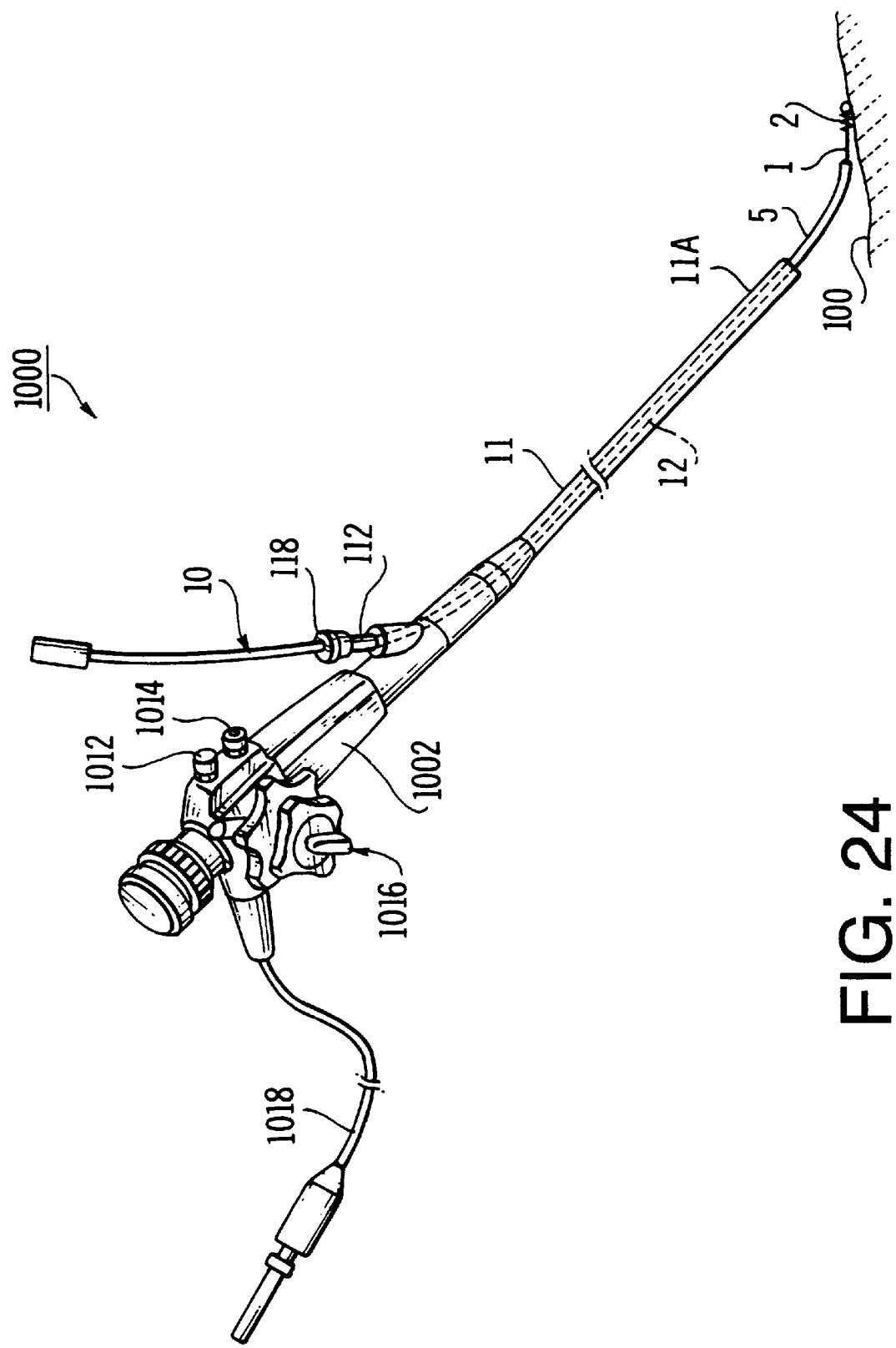
FIG. 24 is a schematic perspective view of an endoscope.

FIG. 24 is a perspective view of the endoscope 1000. The endoscope 1000 includes the main body (manipulation part) 1002. The main body 1002 includes an eye-piece 1010, an air/water feed button 1014, curvature control knobs 1016, a light guide insertion tube 1018, and the forceps channel 12. The insertion part 11, in which a light guide, an image guide or the like (not shown) is enclosed, extends from the main body 1002. The distal end 11A of the insertion part 11 is curved by operation of the curvature control knobs 1016.

In the above-described embodiments, except the seventh, a plurality of openable portions are formed at a distal end of a cover tube. A connecting instrument which eases installation of a cover tube, and particularly of a cover tube formed with a plurality of slits, into the forceps channel 12 of the endoscope 1000 is now described.

A connecting instrument 118 according to an eighth embodiment is detachably coupled to the forceps channel 12. In the description below, the function of the connecting instrument 118 is described in relation to when the brush instrument 10 according to the first embodiment (shown in FIG. 1) is inserted in the forceps channel 12. The brush instrument 10 is inserted through the connecting instrument 118 into the forceps channel 12. The distal end of the brush instrument 10 is to be extended from or retracted into the distal end 11A of the insertion part 11 for the purpose of collecting samples of human tissue 100 or the like.

Figure 25:
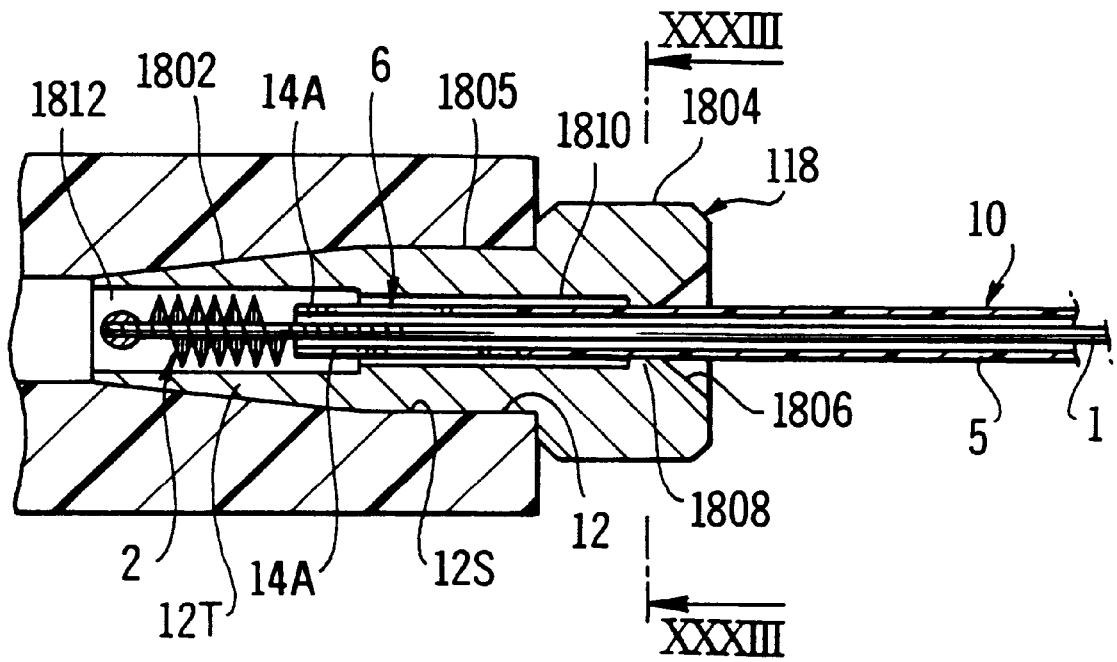
FIG. 25 is a schematic sectional side view of a connecting instrument according to a eighth embodiment.

A cross sectional view of the connecting instrument 118 is shown in FIG. 25. The connecting instrument 118 is made of a material having a predetermined elasticity. The connecting instrument 118 is formed to have a channel side end portion 1802 that has a tapered surface for easier insertion into the forceps channel 12. The other side of the connecting instrument 118 is formed to have an enlarged diameter portion 1804 which can be grasped by an operator when the connecting instrument 118 is removed from or inserted into the forceps channel 12. The forceps channel 12 is formed to have a tapered portion 12T, which corresponds to the tapered portion of the connecting instrument 118.

A cylindrical portion 1805 having a predetermined diameter is formed between the tapered portion 1802 and the enlarged diameter portion 1804.

As shown in FIG. 25, the tapered portion 1802 and the cylindrical portion 1805 are inserted in the forceps channel 12 and the enlarged diameter portion 1804 contacts the end of a surface on which an entrance of the forceps channel 12 is formed. Since the tapered portion 1802 contacts the tapered surface 12T in the forceps channel 12, and the cylindrical portion 1805 contacts a cylindrical inner surface 12S of the forceps channel 12 as shown in FIG. 25, the connecting instrument 118 is firmly coupled to the forceps channel 12. The brush instrument 10 is inserted or removed using the connecting instrument 118 as shown in FIG. 25.

The enlarged diameter portion 1804 includes a tapered inner guide surface 1806 which has a smaller diameter at the inner side of the enlarged diameter portion 1804. A throat portion 1808 is formed inside the enlarged diameter portion 1804. The throat portion 1808 extends from the tapered inner guide surface 1806 and the diameter of the throat portion 1808 is the same as the smallest diameter of the tapered inner guide surface 1806.

The throat portion 1808 has a diameter slightly smaller than the outer diameter of the cover tube 5. Accordingly, when the cover tube 5 is inserted in the cylindrical portion 1806, the outer surface of the cover tube 5 contacts the inner surface of the throat portion 1808 such that a predetermined amount of friction exists between the outer surface of the cover tube 5 and the inner surface of the throat portion 1808. The friction between the outer surface of the cover tube 5 and the inner surface of the throat portion 1808 is such that the cover tube 5 is supported in a stable position when not subjected to external forces but can be moved by application of an external force, for example, manually. In this case, preferably the contact between the outer surface of the cover tube 5 and the inner surface of the throat portion 1808 is airtight such that air does not move between the inner side (i.e., the left-hand side in FIG. 25) and outer side (i.e., the right-hand side in FIG. 26) of the throat portion 1808.

Figure 26:
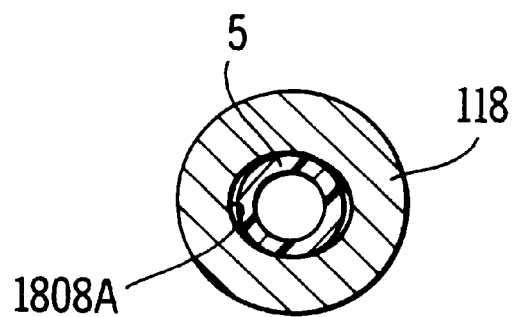
FIG. 26 is a section view of the connecting instrument shown in FIG. 25.

Alternatively, the throat portion 1808 may be formed to have an oval sectional shape 1808A as shown in FIG. 26. In this case, since the cover tube 5 has a tendency to maintain a circular sectional shape, by deforming the shape of the cover tube 5 by the oval-shaped throat portion 1808A, the above-described friction can be achieved. Although the seal is not air-tight in this case, the space is small enough that fluid comes back from the human body.

On the forceps channel side (i.e., on the left-hand side of FIG. 25) of the throat portion 1808, a tube accommodation portion 1810 is formed, and in front of (i.e., on the left-hand side of FIG. 25) the tube accommodation portion 1810, a brush accommodation portion 1812 is formed. These portions form a channel through the connecting instrument 118.

The diameter of the tube accommodation portion 1810 is slightly greater than the outer diameter of the cover tube 5. The length of the tube accommodation portion 1810 is greater than openable portions 14A formed at the distal end of the cover tube 5 by the slits 6. Further, the diameter of the brush accommodation portion 1812 is slightly greater than the diameter of the brush portion 2, and the length of the brush accommodation portion 1812 is greater than the length of the brush portion 2. Thus, in the situation shown in FIG. 27, the cover tube 5 is held such that the openable portions 14A are closed and the brush portion 2 is covered.

Insertion and removal of the brush instrument 10 in the forceps channel 12 using the connecting instrument 118 is now described.

Firstly, the operation wire 1 is inserted through the cover tube 5 until the brush portion 2 protrudes from the distal end of the cover tube 5. Next, the cover tube 5 is inserted in the connecting instrument 118 and the connecting instrument 118 is shifted towards the distal end portion of the cover tube 5 until the openable portions 14A and brush portion 2 are inside the tube accommodation portion 1810 and the brush accommodation portion 1812, respectively.

Preferably, the cover tube 5 is inserted into the connecting instrument 118 by inserting the end of the cover tube 5 that is opposite to the end at which the brush portion 2 is located into the brush accommodation portion 1812. In this way, the openable portions 14A will not be curved or curled up, and insertion can be done more easily. Thus, the brush instrument 10 can be inserted into the connecting instrument 118 easily.

Alternatively, since the guiding portion 1806 is tapered, the openable portions 14A may be relatively easily inserted from the guiding portion 1806 side of the connecting instrument 118.

After the openable portions 14A and brush portion 2 have been accommodated inside the tube accommodation portion 1810 and the brush accommodation portion 1812, respectively, the connecting instrument 118 is inserted into the forceps channel 12 such that the tapered portion 1802 and cylindrical portion 1805 contact the inner surface of the forceps channel 12 and the enlarged diameter portion 1804 contacts the surface at the entrance of the forceps channel 12 in order to position the connecting instrument 118.

Using this method, the connecting instrument 118, the cover tube 5 and the operation wire 1 are concentrically aligned within the forceps channel 12. Thereafter, the insertion part 11 of the endoscope 1000 is inserted in a human cavity, and then the brush instrument 10 is pushed through the forceps channel 12 by a desired amount so that the cover tube 5 and the brush portion 2 accommodated therein protrudes from the distal end portion 11A of the insertion part 11 and the brush portion 2 is then extended from the cover tube 5 and moved to a desired position.

After a substance is collected, the brush portion 2 carrying the substance is accommodated inside the openable portions 14A of the cover tube 5 as described above.

Figure 27:
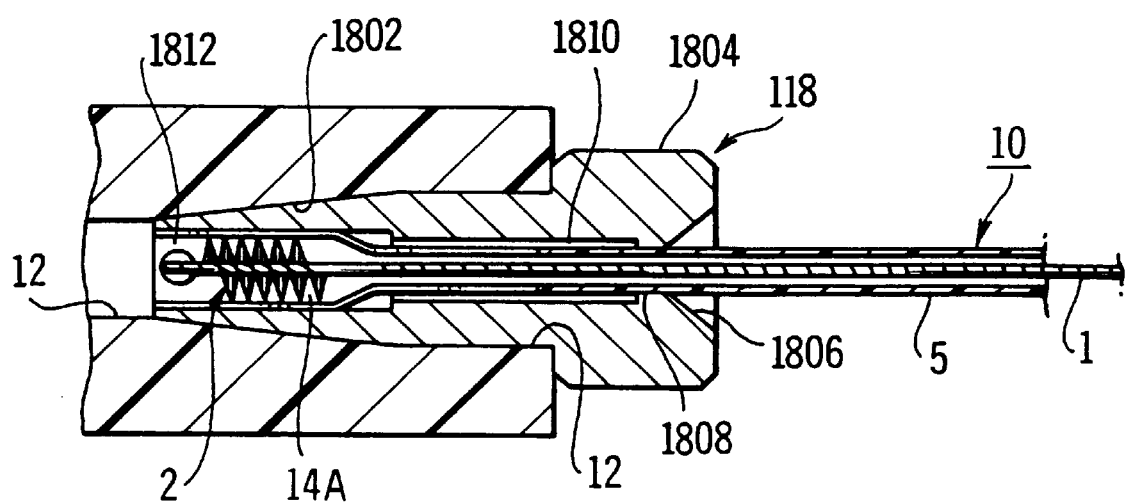
FIG. 27 is a schematic sectional side view of the connecting instrument shown in FIG. 25 in a different state.

Next, the brush instrument 10 is pulled back such that the openable portions 14A of the cover tube 5 is located at the brush accommodation portion 1812 as shown in FIG. 27. In this situation, the openable portions 14A may be pushed by the inner wall of the brush accommodation portion 1812 to have a slightly reduced diameter.

When the brush instrument 10 is positioned as shown in FIG. 27, the connecting instrument 118 and the brush instrument 10 are removed from the forceps channel 12 together.

According to the above-described eighth embodiment, insertion of the brush instrument 10 provided with the cover tube 5 having the plurality of openable portions 14A at its distal end can be easily inserted into a forceps channel 12 without damaging or curling the openable portions 14A. Further, when the brush instrument 10 is removed from the forceps channel, the diameter of the brush portion 2 does not need to be reduced very much and the brush portion 2 is protected by the openable portions 14A of the cover tube 5 and the connecting instrument 118. Thus, this arrangement is advantageous for collecting a large quantity of cells or the like.

Figure 28:
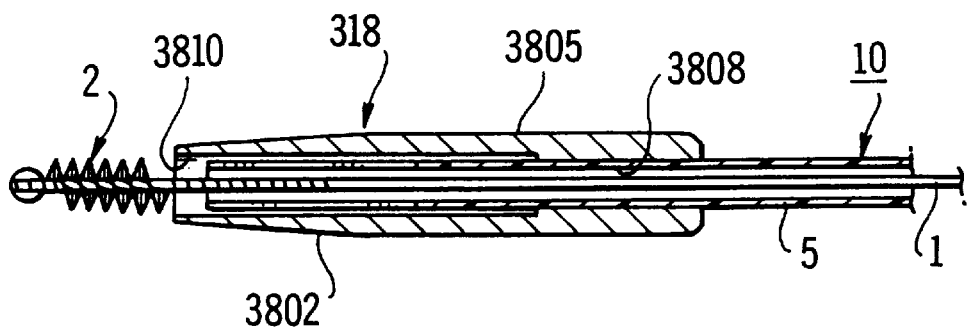
FIG. 28 is a schematic sectional side view of a connecting instrument according to an ninth embodiment.

FIG. 28 shows a connecting instrument 318 according to a ninth embodiment.

The connecting instrument 318 is different from the connecting instrument 118 in that the enlarged diameter portion 1804 and the brush accommodation portion 1812 are omitted.

As shown in FIG. 28, the connecting instrument 318 has the tapered surface 3802, similar to the tapered surface 1802 of the seventh embodiment, and a cylindrical portion 3805, having a predetermined outer diameter. Inside the connecting instrument 318, a throat portion 3808 and a tube accommodation portion 3810 are formed.

Since the connecting instrument 318 has a slender shape, it is particularly applicable for a forceps channel having a relatively a small diameter.

Figure 29:
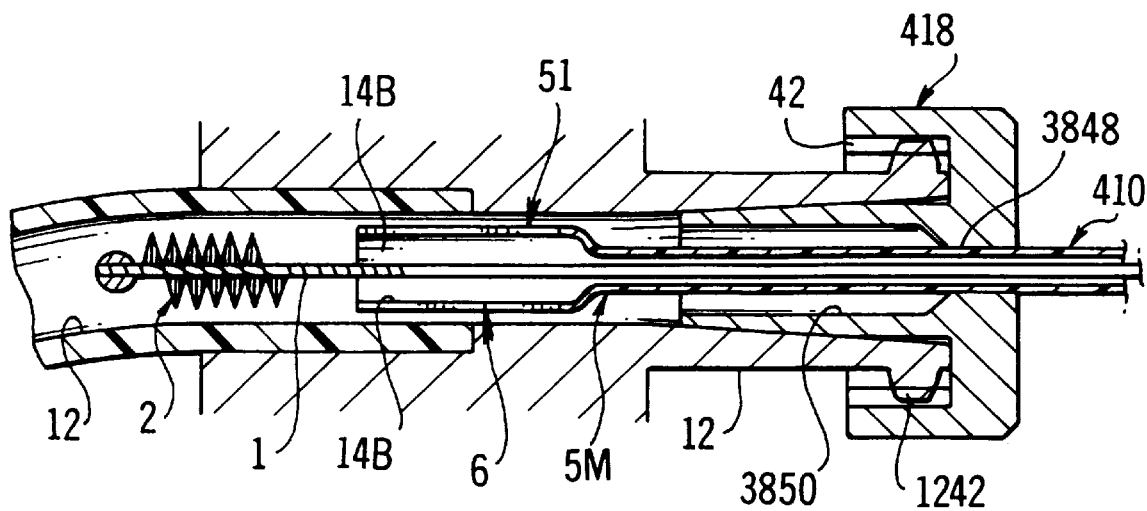
FIG. 29 is a schematic sectional side view of a connecting instrument according to a tenth embodiment.

FIG. 29 shows a connecting instrument 418 according to a tenth embodiment.

The connecting instrument 418 has a box-nut like screw portion 42 around a proximal end thereof. Further, at the entrance of the forceps channel 12, a screw thread 1242 is formed to engage with the screw portion 42. By screwing the screw portion 42 on the screw thread 1242, the connecting instrument 418 is fixed to the forceps channel 12.

In the tenth embodiment, a brush instrument 410 includes an operation wire 1 and a brush portion 2, which are similar to the brush instrument 10, and further a cover tube 5M. The cover tube 5M is similar to the second embodiment (shown in FIG. 8), and has an enlarged diameter portion 51 at the distal end thereof. The enlarged diameter portion 51 is formed having a plurality of slits 6 and is divided into a plurality of openable portions 14B. The enlarged diameter portion 51 is for accommodating the brush portion 2 when the brush portion 2 is carrying the substance to be collected. The length of the enlarged diameter portion 51 (i.e., the length of the openable portions 14B) is greater than the length of the brush portion 2 so that the brush portion 2 can be completely accommodated in the enlarged diameter portion 51.

Corresponding to the shape of the enlarged diameter portion 51, the inside of the connecting instrument 418 is provided with an accommodation portion 3850. A throat portion 3848 is also formed to allow the cover tube 5M to pass through the connecting instrument 418. The inner diameter of the accommodation portion 3850 is slightly greater than the outer diameter of the enlarged diameter portion 51 of the cover tube 5M.

The above-described embodiments are directed to cytology brush instruments that are provided with a cover tube 5, 5M having slits 6. However, the concepts described can be applied to any treatment accessory which is used for collecting material, such as tissue, cells, mucous and the like. As an example of a treatment accessory other than a brush instrument, a grasping instrument is now described.

Figure 30:
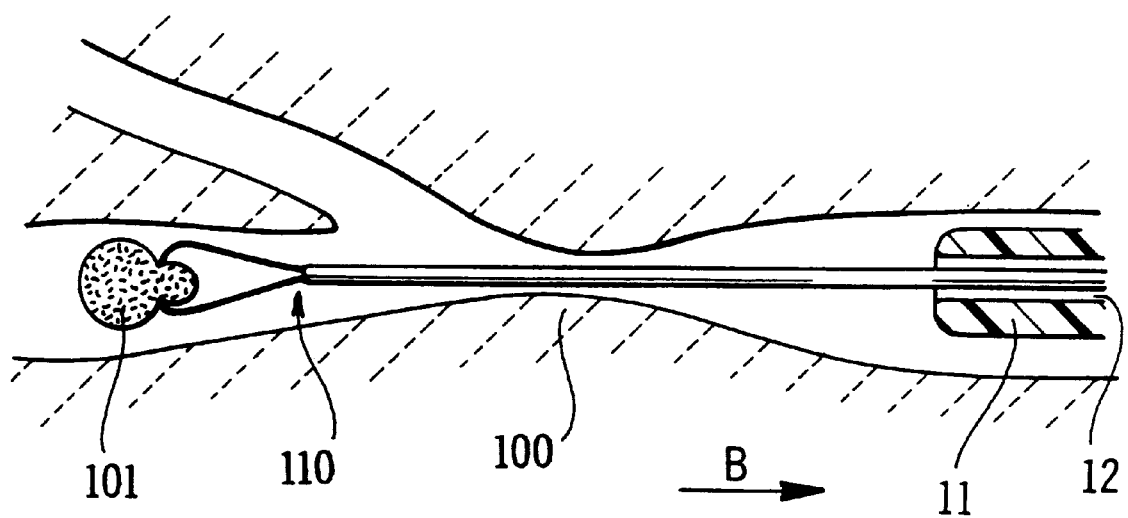
FIG. 30 is a schematic sectional side view of a conventional grasping forceps instrument shown inside a human body.

FIG. 30 shows a conventional grasping forceps 110 which is used for collecting material 101 from inside a human body 100. The grasping forceps 110, when in use, is inserted in the forceps channel 12 of the endoscope 1000. Similar to the problem of collecting cells described above, when the grasping forceps 110 is moved in the direction of the arrow B and drawn into the distal end of the insertion part 11 of the endoscope 1000 (cf. FIG. 3), the material 101 grasped by the grasping forceps 110 or a portion thereof may be knocked away from the forceps 110 by the other parts of the human tissue or at the forceps channel 12.

Figure 31:
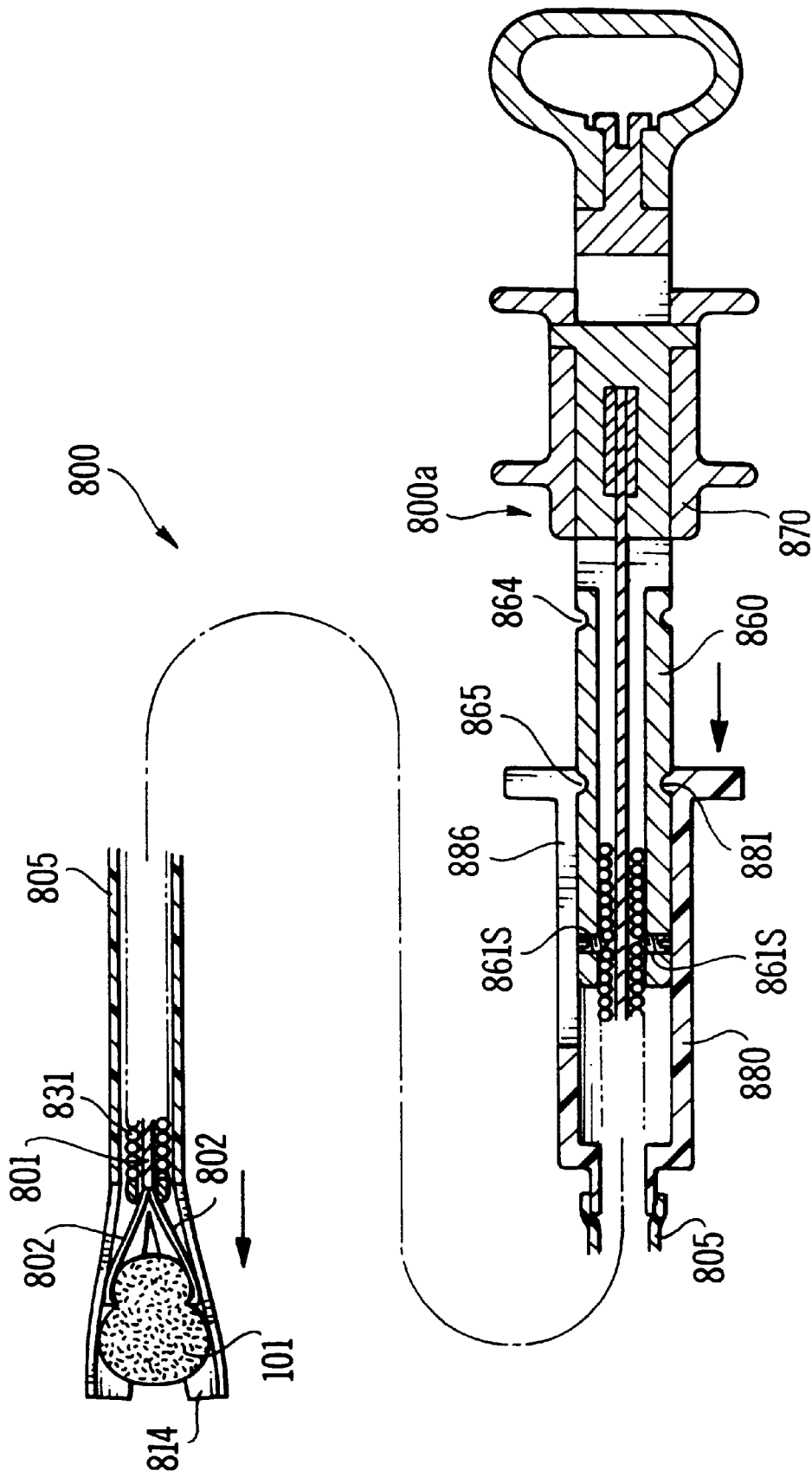
FIG. 31 is a schematic sectional side view of a grasping forceps instrument according to an eleventh embodiment.

FIG. 31 shows a grasping forceps instrument 800 according to an eleventh embodiment of the invention. With use of the grasping forceps instrument 800, the above-described problem of the conventional art can be avoided.

The grasping forceps instrument 800 has a flexible tube 831 which is to be inserted in a forceps channel 12 of an endoscope (shown in FIG. 3). The flexible tube 831 is, for example, a coil formed by closely winding a stainless steel wire. An operation wire 801 is movably inserted inside the flexible tube 831. At a distal end (i.e., left-hand end in FIG. 31) of the operation wire 801, a pair of grasping forceps 802 are connected.

Figure 32:
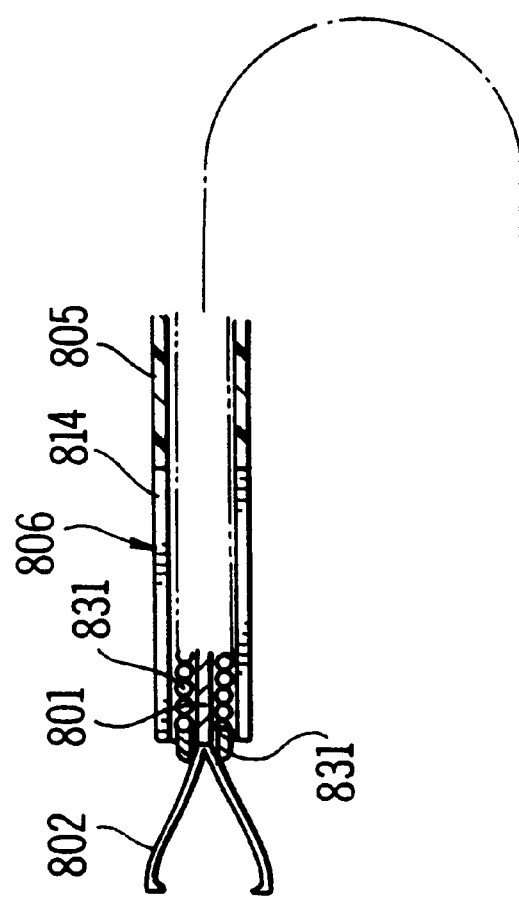
FIG. 32 is a schematic sectional side view of the grasping forceps instrument shown in FIG. 31 in a different state.
Figure 32:
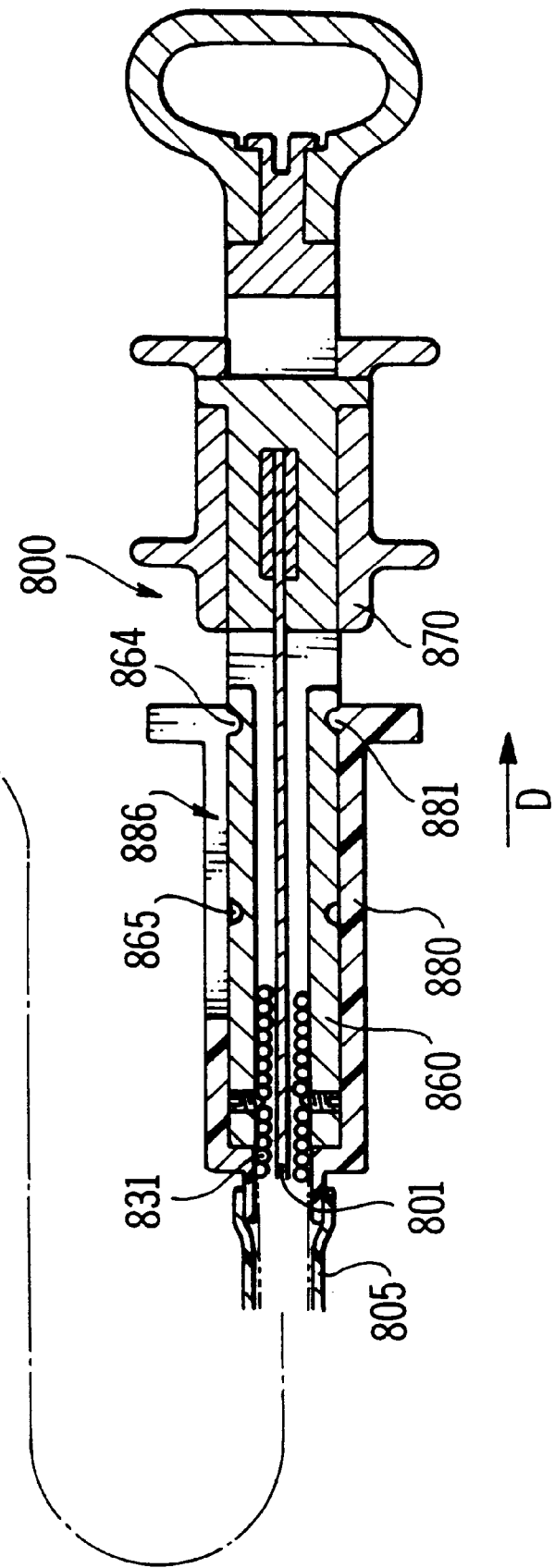

In the eleventh embodiment, the grasping forceps 802 are made of plate spring such that when the grasping forceps 802 is moved to protrude from the flexible tube 831, the grasping forceps 802 open with elastic force as shown in FIG. 32. Conversely, when the operation wire 801 is pulled (i.e., moved in the direction of arrow C with respect to the flexible tube 831), the grasping forceps 802 are folded (closed) by contact with the flexible tube 831.

The proximal ends (i.e., manipulation side ends, at the left side in FIG. 31) of the flexible tube 831 and the operation wire 801 are connected to a manipulation portion 800a. The proximal end of the flexible tube 831 is fixed to a first slider 860 of the manipulation portion 800a with screws 861S. The proximal end of the operation wire 801 is fixed to a second slider 870 which is fitted on the first slider 860. The first slider 860 is engaged with a main body 880.

By slidably moving the second slider 870 relative to the first slider 860, the operation wire 801 can slide relative to the flexible tube 831. As the operation wire 801 slides inside the flexible tube 831, the grasping forceps 802 are protected from or retracted into the flexible tube 831 and are thus opened or closed. In this way, an operator controls the grasping forceps 802 to open or close.

A cover tube 805 is provided surrounding the flexible tube 831 and is attached to the main body 880. The cover tube 805 is formed to be flexible having a certain elasticity. The flexible tube 831 is slidable inside the cover tube 805. The cover tube 805 is made of fluorocarbon resin in the embodiment, although polyethylene, polyurethane, polyimide or the like can also be used.

When the first slider 860 is fully inserted into the main body 880, the distal end of the flexible tube 831 is located at the distal end of the cover tube 805 as shown in FIG. 32. At the distal end portion of the cover tube 805, four slits 806 each extending along the axial direction of the cover tube 805 are formed. The four slits 806 are arranged around the circumferential surface of the cover tube spaced by approximately 90 degrees. In other words, the end portion of the cover tube 805 is divided into four portions by the slits 806. The length of the slits 806 is approximately 1.5 to 2.5 times as long as the length of the grasping forceps 802 in the direction of the operation wire 801.

A plurality of click protrusions 881 are formed at a predetermined position on the inner surface of the main body 880. Corresponding to the click protrusions 881, a first engaging groove 864, and a second engaging groove 865 are formed on the outer surface of the first slider 860. The first and second engaging grooves 864 and 865 are separated by a predetermined distance in the axial direction. Specifically, the distance between the first and second engaging grooves 864 and 865 is substantially the same as the length of the slits 806.

Figure 33:
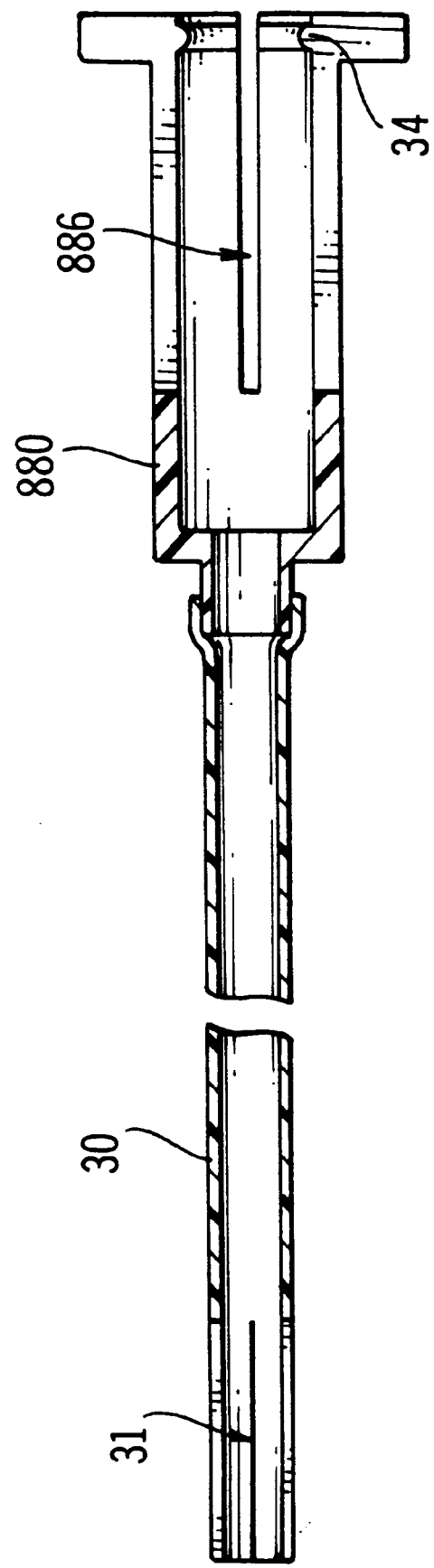
FIG. 33 is a schematic sectional side view of a main body and a cover tube of the grasping forceps instrument shown in FIG. 31.

The main body 880 has a shape similar to that of a syringe barrel, and is formed to include a plurality of slits 886 extending in the axial direction thereof. The slits 886 allow the portion of the main body 880 where the click protrusions 881 are formed to be shiftable in an outward direction from the axis of the main body 880. In this way, the first slider 860 can be moved within the main body 880 so that the click protrusions 881 can be engaged with either the first engaging groove 864 or the second engaging groove 865. This arrangement of the main body 880 also allows the first slider 860 and the flexible tube 831 to be completely removed from the main body 880 and the cover tube 805. The structure of the main body 880 and the cover tube 805 after removal of the flexible tube 831 is shown in FIG. 33.

As shown in FIG. 32, when the main body 880 is located at a position where the click protrusions 881 are engaged with the first engaging groove 864, the distal end of the flexible tube 831 is located substantially at the distal end of the cover tube 805.

When the first slider 860 is operated to slide in the direction of arrow D in FIG. 32 relative to the main body 880, and the click protrusions 881 engage with the second engaging groove 865 as shown in FIG. 31, the flexible tube 831 is drawn inside the cover tube 805 such that the grasping forceps 802 together with the grasped material 101 are completely retracted inside the cover tube 805.

When the grasping forceps 802 are pulled into the distal end of the cover tube 805 (i.e., pulled towards the right-hand side in FIG. 32 by movement of the first slider 860), if the grasping forceps 802 are holding some material 101, since the slits 806 are formed at the end portion of the cover tube 805, the end portion of the cover tube 805 is pushed to open by the grasping forceps 802. Accordingly, as shown in FIG. 31, the grasping forceps 802 and the material 101 are enclosed by the slitted portion (openable portion) 814 of the cover tube 805.

Figure 34:
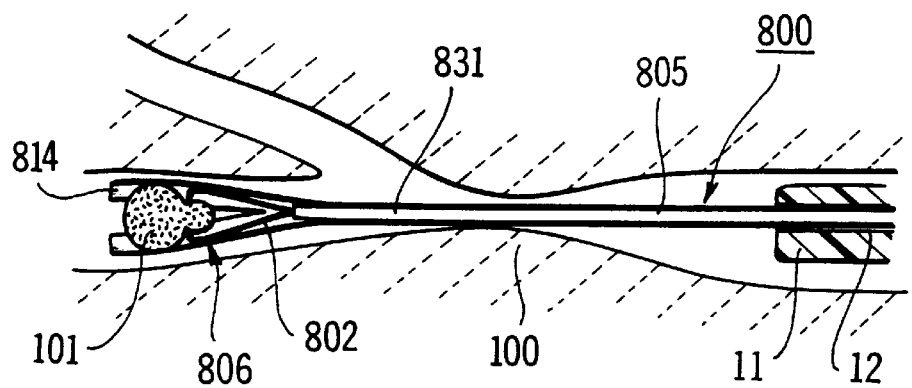
FIG. 34 is a schematic sectional side view of the grasping forceps instrument shown in FIG. 31 in operation.

The grasping forceps instrument 800 constructed as above is used as shown in FIG. 34. The grasping forceps instrument 800 it inserted through a forceps channel 12 of an insertion part 11 of an endoscope. Firstly, the grasping forceps 802 are projected from both the flexible tube 831 and the cover tube 805. The material 101 to be collected is grasped by the grasping forceps 802 and then the grasped material 101 and the grasping forceps 802 are both enclosed in the end portion of the cover tube 805 by moving the flexible tube 831 relative to the cover tube 805 (in the right-hand direction in FIG. 34). Thereafter, the grasping forceps instrument 800 is retracted as a whole through the forceps channel 12 of the endoscope. Since the grasping forceps 802 as well as the grasped material 101 are retracted and enclosed in the cover tube 805, the material 101 is less likely to be torn off, or fall from the grasping forceps 802 even when passing through a narrow portion of the human body 100 or when entering or moving through the forceps channel 12.

It should be noted that the number of the slits 806 formed at the end portion of the cover tube 805 is not necessarily limited to four, but can be any number greater than one.

Figure 35:
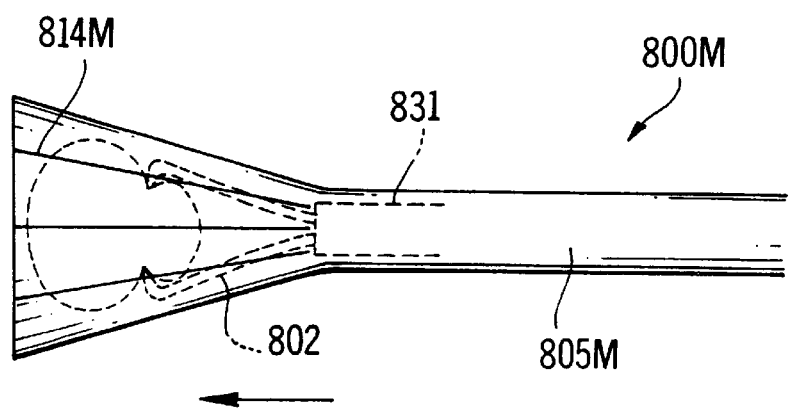
FIG. 35 is a schematic view of a variation of the grasping forceps instrument of FIG. 31.
Figure 36:
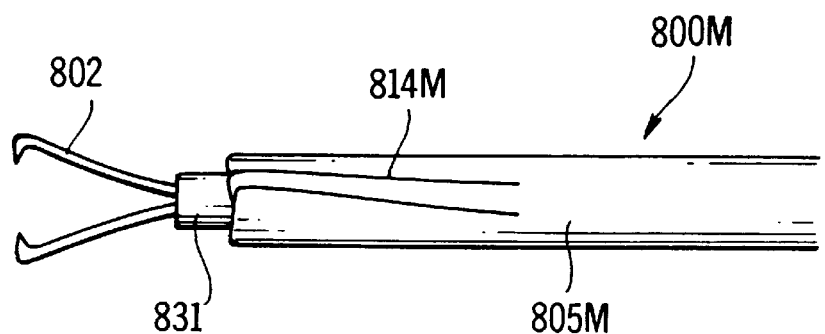
FIG. 36 is a schematic view of the variation of the grasping forceps instrument shown in FIG. 35.

In a variation of this embodiment, as shown in FIGS. 35 and 36, an end portion of a cover tube 805M is formed having a funnel shape which is divided such that the funnel shape is able to fold inward as shown in FIG. 36. With this type of funnel shape, as the material 101 and grasping forceps 802 are drawn into the cover tube 805, there are no gaps or openings around the end portion of the cover tube 805M as there might be when the slits 806 are used.

It should be noted that, the above embodiments have been described in relation to a cytology brush instrument and a grasping forceps instrument, however, each of the embodiments may be applied according to the type of treatment accessory being designed. For example, if necessary, the grasping forceps instrument 800 shown in FIG. 31 may be provided with a sheath similar to that of the cytology brush instrument 300 according to the third embodiment (shown in FIG. 12) in order to keep the grasping forceps 802 centered with respect to the cover tube 805.

It should further be noted that, in the above described embodiments, connecting instruments are described in relation to a brush instrument having a cover tube on which openable portions are formed. However, even if the cover tube has a different structure, the above described structure of the connecting instruments may be applicable. Further, the connecting instrument can also be used for inserting other instruments into the forceps channel.

Since the cover tube is easily pre-installed in the connecting instrument without deforming the openable portions, the cover tube can be easily inserted in the forceps channel merely by coupling the connecting instrument onto the forceps channel and pushing the cover tube.

The present disclosure relates to subject matter contained in Japanese Patent Applications Nos. HEI 07-110994 filed on May 10, 1995, HEI 07-116798 filed on May 16, 1995, HEI 07-116799 filed on May 16, 1995, HEI 07-311622 filed on Nov. 6, 1995 and HEI 07-311623 filed on Nov. 6, 1995, which are expressly incorporated herein by reference in their entirety.

What is claimed is:

1. A treatment apparatus for use with an endoscope, said treatment apparatus being inserted into a forceps channel of said endoscope, said treatment apparatus comprising:
    a flexible element;
    a treatment instrument connected to a distal end of said flexible element; and
    a cover tube having distal and proximal ends, said treatment instrument and said flexible element being slidably received in said cover tube, said distal end of said cover tube including at least one longitudinal slit extending to and opening at said distal end, said distal end expanding to receive said treatment instrument.

2. The treatment apparatus according to claim 1, wherein said treatment instrument is a cytology brush.

3. The treatment apparatus according to claim 2, said cytology brush comprising a bristle portion having bristles, a proximal end adjacent to the flexible element, and a distal end, the diameter of the bristles at said proximal end being larger than the diameter of the bristles at said distal end.

4. The treatment apparatus according to claim 1, wherein said treatment instrument is a forceps.

5. The treatment apparatus according to claim 1, the length of said at least one longitudinally extending slit being longer than the length of said treatment instrument.

6. The treatment apparatus according to claim 1, the distal end of said cover tube including a plurality of longitudinally extending slits.

7. The treatment apparatus according to claim 6, the distal end of said cover tube including three longitudinally extending slits.

8. The treatment apparatus according to claim 6, the distal end of said cover tube including four longitudinally extending slits.

9. The treatment apparatus according to claim 1, wherein the diameter of said distal end of said cover tube is larger than the diameter of the remainder of said cover tube.

10. The treatment apparatus according to claim 1, wherein said distal end of said cover tube is funnel-shaped when expanded.

11. The treatment apparatus according to claim 1, further comprising a sheath surrounding said flexible element, wherein said sheath locates said flexible element at substantially the radial center of said cover tube.

12. The treatment apparatus according to claim 11, wherein said sheath is of a material having a low friction coefficient.

13. The treatment apparatus according to claim 11, wherein said sheath extends along substantially the entire length of said flexible element.

14. The treatment apparatus according to claim 11, wherein said sheath is provided at only a distal end portion of said flexible element.

15. The treatment apparatus according to claim 1, further comprising a connecting instrument being inserted into said forceps channel, said treatment instrument, said flexible element, and said cover tube being inserted into a throat portion of said connecting instrument.

16. The treatment apparatus according to claim 15, wherein an inner diameter of said throat portion is less than an outer diameter of said cover tube, whereby a predetermined amount of friction exists between the outer surface of said cover tube and the inner surface of said throat portion.

17. The treatment apparatus according to claim 15, wherein said throat portion has an oval cross-sectional shape and said cover tube has a circular cross-sectional shape, whereby a predetermined amount of friction exists between the outer surface of said cover tube and the inner surface of said throat portion.

18. The treatment apparatus according to claim 15, said connecting instrument further comprising a treatment instrument accommodation portion, a diameter of said accommodation portion being greater than a diameter of said treatment instrument.

19. A connecting instrument in combination with an endoscope, said connecting instrument being inserted into and coupled to a forceps channel of said endoscope for receipt of a treatment instrument being connected to a flexible element, said flexible element being surrounded by a cover tube, said connecting instrument comprising:
    a throat portion for receipt of said treatment instrument, said flexible element and said cover tube being inserted into said throat portion of said connecting instrument, a predetermined amount of friction existing between the outer surface of said cover tube and the inner surface of said throat portion, wherein said cover tube is held in a stable position with respect to said throat portion and can be moved when subjected to an external force.

20. The connecting instrument according to claim 19, wherein an inner diameter of said throat portion is less than an outer diameter of said cover tube.

21. The connecting instrument according to claim 19, wherein said throat portion has an oval cross-sectional shape and said cover tube has a circular cross-sectional shape.

22. The connecting instrument according to claim 19, said connecting instrument further comprising a treatment instrument accommodation portion, a diameter of said accommodation portion being greater than a diameter of said treatment instrument.

23. A treatment apparatus for use with an endoscope, said treatment apparatus being inserted into a forceps channel of said endoscope, said treatment apparatus comprising:
    a flexible element;
    a treatment instrument connected to a distal end of said flexible element;
    a cover tube having distal and proximal ends, said treatment instrument and flexible element being slidably received in said cover tube, said distal end of said cover tube including at least one longitudinal slit extending to and opening at said distal end, said distal end expanding to receive said treatment instrument; and a sheath surrounding said flexible element, wherein said sheath locates said flexible element at substantially the radial center of said cover tube.

24. The treatment apparatus according to claim 23, wherein said sheath is of a material having a low friction coefficient.

25. The treatment apparatus according to claim 23, wherein said sheath extends along substantially the entire length of said flexible element.

26. The treatment apparatus according to claim 23, wherein said sheath is provided at only a distal end portion of said flexible element.

27. A connecting instrument for use with an endoscope, said connecting instrument being inserted into a forceps channel of said endoscope for receipt of a treatment instrument being connected to a flexible element, said flexible element being surrounded by a cover tube, said connecting instrument comprising:

a throat portion for receipt of said treatment instrument, said flexible element and said cover tube being inserted into said throat portion of said connecting instrument, wherein said throat portion has an oval cross-sectional shape and said cover tube has a circular cross-sectional shape, whereby a predetermined amount of friction exists between an outer surface of said cover tube and the inner surface of said throat portion.

28. A treatment apparatus for use with an endoscope, said treatment apparatus being inserted into a forceps channel of said endoscope, said treatment apparatus comprising:

a flexible element;

a treatment instrument connected to a distal end of said flexible element;

a cover tube having distal and proximal ends, said treatment instrument and flexible element being slidably received in said cover tube; and a sheath surrounding said flexible element, said sheath being provided at only a distal end portion of said flexible element, wherein said sheath locates said flexible element at substantially the radial center of said cover tube.

* * * * *